US009023365B2

(12) United States Patent
Yoshida et al.

(10) Patent No.: US 9,023,365 B2
(45) Date of Patent: May 5, 2015

(54) RECOMBINANT BACULOVIRUS VACCINE

(75) Inventors: Shigeto Yoshida, Shimotsuke (JP);
Yoshio Ohba, Tokushima (JP);
Norimitsu Hariguchi, Tokushima (JP);
Masami Mizukoshi, Tokushima (JP);
Masanori Kawasaki, Tokushima (JP);
Makoto Matsumoto, Tokushima (JP);
Yoshihiro Goto, Tokushima (JP)

(73) Assignees: Educational Foundation Jichi Medical University, Tochigi (JP); Otsuka Pharmaceutical Co., Ltd., Tokyo (JP)

( * ) Notice: Subject to any disclaimer, the term of this patent is extended or adjusted under 35 U.S.C. 154(b) by 557 days.

(21) Appl. No.: 12/278,916

(22) PCT Filed: Feb. 8, 2007

(86) PCT No.: PCT/JP2007/052195
§ 371 (c)(1),
(2), (4) Date: Aug. 8, 2008

(87) PCT Pub. No.: WO2007/091624
PCT Pub. Date: Aug. 16, 2007

(65) Prior Publication Data
US 2010/0233202 A1 Sep. 16, 2010

(30) Foreign Application Priority Data
Feb. 9, 2006 (JP) .................................. 2006-32863

(51) Int. Cl.
C12N 15/62 (2006.01)
C12N 15/866 (2006.01)
A61K 39/015 (2006.01)
C12N 15/86 (2006.01)
A61K 39/04 (2006.01)
A61K 39/145 (2006.01)
C07K 14/005 (2006.01)
A61K 39/00 (2006.01)

(52) U.S. Cl.
CPC .............. *C12N 15/86* (2013.01); *A61K 39/015* (2013.01); *A61K 39/04* (2013.01); *A61K 39/145* (2013.01); *A61K 2039/525* (2013.01); *C07K 14/005* (2013.01); *C07K 2319/02* (2013.01); *C07K 2319/43* (2013.01); *C12N 2710/14143* (2013.01); *C12N 2760/16134* (2013.01); *C12N 2830/205* (2013.01); *A61K 39/00* (2013.01); *A61K 2039/5256* (2013.01); *A61K 2039/543* (2013.01); *A61K 2039/544* (2013.01)

(58) Field of Classification Search
None
See application file for complete search history.

(56) References Cited

U.S. PATENT DOCUMENTS

| 4,879,236 | A | 11/1989 | Smith et al. |
|---|---|---|---|
| 5,168,062 | A | 12/1992 | Stinski |
| 5,169,784 | A | 12/1992 | Summers et al. |
| 5,385,839 | A | 1/1995 | Stinski |
| 5,753,220 | A | 5/1998 | Suzuki et al. |
| 5,762,939 | A | 6/1998 | Smith et al. |
| 5,770,400 | A | 6/1998 | Miyazaki et al. |
| 5,811,260 | A | 9/1998 | Miyazaki et al. |
| 5,858,368 | A | 1/1999 | Smith et al. |
| 5,976,552 | A | 11/1999 | Volvovitz |
| 6,103,526 | A | 8/2000 | Smith et al. |
| 6,183,993 | B1 | 2/2001 | Boyce et al. |
| 6,190,887 | B1 | 2/2001 | Boyce et al. |
| 6,245,532 | B1 | 6/2001 | Smith et al. |
| 6,338,953 | B1 | 1/2002 | Boyce et al. |
| 6,485,729 | B1 | 11/2002 | Smith et al. |
| 6,589,783 | B2 * | 7/2003 | Novy et al. ................. 435/320.1 |
| 6,607,912 | B2 | 8/2003 | Blissard et al. |
| 6,716,823 | B1 | 4/2004 | Tang et al. |
| 6,793,926 | B1 | 9/2004 | Rasty et al. |
| 6,858,205 | B2 | 2/2005 | Blissard et al. |
| 6,951,649 | B2 | 10/2005 | Smith et al. |
| 7,722,889 | B2 | 5/2010 | Duffy et al. |
| 2002/0071848 | A1 | 6/2002 | Smith et al. |
| 2003/0045492 | A1 | 3/2003 | Tang et al. |
| 2003/0104580 | A1 | 6/2003 | Inaba et al. |
| 2003/0125278 | A1 | 7/2003 | Tang et al. |
| 2004/0009153 | A1 | 1/2004 | Blissard et al. |
| 2004/0009936 | A1 | 1/2004 | Tang et al. |
| 2004/0071733 | A1 | 4/2004 | Takaku et al. |
| 2005/0009184 | A1 | 1/2005 | Maitland |
| 2005/0019928 | A1 | 1/2005 | Rasty et al. |
| 2005/0064557 | A1 | 3/2005 | Inaba et al. |
| 2005/0208066 | A1 | 9/2005 | Chao et al. |
| 2005/0208661 | A1 | 9/2005 | Matsuura |
| 2006/0183231 | A1 | 8/2006 | Pachuk et al. |
| 2007/0042977 | A1 | 2/2007 | Ertl |
| 2010/0233202 | A1 | 9/2010 | Yoshida et al. |
| 2011/0159034 | A1 | 6/2011 | McMichael et al. |

FOREIGN PATENT DOCUMENTS

| JP | 3366328 B2 | 1/2002 |
|---|---|---|
| JP | 2002-253263 A | 9/2002 |
| JP | 2003-284557 A | 10/2003 |

(Continued)

OTHER PUBLICATIONS

Yoshida et al. Virology 2003 vol. 316, pp. 161-170.*
European Search Report dated Oct. 29, 2009 issued in European Application No. EP 07 70 8219.
K. M. Lima, et al, "Single dose of a vaccine based on DNA encoding mycobacterial hsp65 protein plus TDM-loaded PLGA microspheres protects mice against a virulent strain of *Mycobacterium tuberculosis*", Gene Therapy, Macmillan Press Ltd., vol. 10, No. 8, pp. 678-685, Apr. 1, 2003.

(Continued)

*Primary Examiner* — Mary E Mosher
*Assistant Examiner* — Myron Hill
(74) *Attorney, Agent, or Firm* — Sughrue Mion, PLLC

(57) ABSTRACT

A recombinant transfer vector capable of expressing a foreign gene fused to a viral gene under the control of dual promoters and a recombinant baculovirus, and methods for production thereof, as well as pharmaceuticals comprising the recombinant baculovirus as an active ingredient.

5 Claims, 13 Drawing Sheets

(56) References Cited

FOREIGN PATENT DOCUMENTS

| | | |
|---|---|---|
| JP | 2005-15346 A | 1/2005 |
| JP | 2006180865 A | 7/2006 |
| JP | 2007023044 A | 2/2007 |
| TW | 200804597 A | 1/2008 |
| WO | 9526982 A2 | 10/1995 |
| WO | 96/33738 A1 | 10/1996 |
| WO | 96/37624 A1 | 11/1996 |
| WO | 98/11243 A3 | 3/1998 |
| WO | 98/46262 A1 | 10/1998 |
| WO | 98/55640 A1 | 12/1998 |
| WO | 99/09193 A1 | 2/1999 |
| WO | 00/66179 A1 | 11/2000 |
| WO | 00/73480 A1 | 12/2000 |
| WO | 02/14527 A2 | 2/2002 |
| WO | 02/062381 A1 | 8/2002 |
| WO | 03/016450 A1 | 2/2003 |
| WO | 03/020322 A1 | 3/2003 |
| WO | 03/070920 A1 | 8/2003 |
| WO | 2004/029259 A1 | 4/2004 |
| WO | 2004/041852 A2 | 5/2004 |
| WO | 2005/040388 A2 | 5/2005 |
| WO | 2006/056753 A2 | 6/2006 |
| WO | 2007027860 A2 | 3/2007 |
| WO | 2007037265 A1 | 4/2007 |

OTHER PUBLICATIONS

Singapore Search Report dated Oct. 27, 2009 issued in Singapore Application No. 200805080-9.

K. Kojima et al., "Tandem repetition of baculovirus ie1 promoter results in upregulation of transcription", Arch Virol (2001) 146: pp. 1407-1414.

Hideki Tani et al., "Characterization of Cell-Surface Determinants Important for Baculovirus infection", Virology 279, pp. 343-353 (2001).

Andrea Facciabene, et al., "Baculovirus Vectors Elicit Antigen-Specific Immune Responses in Mice", Journal of Virology, vol. 78, No. 16, Aug. 2004, pp. 8663-8672.

Luisa Pieroni et al., In Vivo Gene Transfer in Mouse Skeletal Muscle Mediated by Baculovirus Vectors, Human Gene Therapy 12: pp. 871-881 (May 20, 2001).

Yu-Chen Hu, "Baculovirus Vectors for Gene Therapy", Advances in Virus Research, vol. 68, pp. 287, 296, & 298, 2006.

David R. O'Reilly, et al., "Baculovirus Expression Vectors", A Laboratory Manual, pp. 41-46; Oxford University Press, 1994.

Christian Hofmann et al., "Efficient gene transfer into human hepatocytes by baculovirus vectors", Proc. Natl. Acad. Sci. USA, vol. 92, pp. 10099-10103, Oct. 1995.

Frederick M. Boyce et al., "Baculovirus-mediated gene transfer into mammalian cells", Proc. Natl. Acad. Sci. USA, vol. 93, pp. 2348-2352, Mar. 1996.

Boublik, Y. et al., "Eukaryotic Virus Display: Engineering the Major Surface Glycoprotein of the *Autographa califomica* Nuclear Polyhedrosis Virus (AcNPV) for the Presentation of Foreign Proteins on the Virus Surface", Biotechnology, vol. 13, pp. 1079-1084, Oct. 13, 1995.

Bingke Bai et al., "Vaccination of mice with recombinant baculovirus expressing spike or nucleocapsid protein of SARS-like coronavirus generates humoral and cellular immune responses", Molecular Immunology 45 (2008) pp. 868-875.

Strauss, R., et al., "Baculovirus-based Vaccination Vectors Allow for Efficient Induction of Immune Responses Against *Plasmodium falciparum* Circumsporozoite Protein", Molecular Therapy, vol. 15, No. 1, pp. 193-202, Jan. 2007.

Liqun Lu et. al., "Baculovirus surface-displayed hemagglutinin of H5N1 influenza virus sustains its authentic cleavage, hemagglutination activity, and antigenicity", BBRC. 358 (2007), pp. 404-409.

Kuie-Chun Wang et al., "Baculovirus as a Highly Efficient Gene Delivery Vector for the Expression of Hepatitis Delta Virus Antigens in Mammalian Cells", Biotechnology and Bioengineering, vol. 89, No. 4, pp. 464-473, Feb. 20, 2005.

L. Ikonomou et al., "Insect cell culture for industrial production of recombinant proteins", Appl. Microbiol Biotechnol., 62, pp. 1-20, (2003).

John J. Davis et al., "Oncolysis and Suppression of Tumor Growth by a GFP-Expressing Oncolytic Adenovirus Controlled by an hTERT and CMV Hybrid Promoter", Cancer Gene Ther., vol. 13, No. 7, pp. 720-723, Jul. 2006.

R. Grabherr et al., "Developments in the use of baculoviruses for the surface display of complex eukaryotic proteins", Trends in Biotechnology, vol. 19, No. 6, pp. 231-236, Jun. 2001.

J.T. Mangor et al., "A GP64-Null Baculovirus Pseudotyped with Vesicular Stomatitis Virus G Protein", Journal of Virology, vol. 75, No. 6, pp. 2544-2556, Mar. 2001.

J.P. Condreay et al., "Transient and stable gene expression in mammalian cells transduced with a recombinant baculovirus Vector", Proc. Natl. Acad. Sci. USA, vol. 96, pp. 127-132, Jan. 1999.

Ying Li et al., "Neuronal gene transfer by baculovirus-derived vectors accommodating a neurone-specific promoter", Exp. Physiol., vol. 90, No. 1, pp. 39-44, (2004).

Dung-Fang Lee et al., "A Baculovirus Superinfection System: Efficient Vehicle for Gene Transfer into *Drosophila* S2 Cells", Journal of Virology, vol. 74, No. 24, pp. 11873-11880, Dec. 2000.

Yoshida, S. et al., "Baculovirus virions displaying *Plasmodium berghei* circums porozoite protein protect mice against malaria sporozoite infection", Virology, vol. 316, pp. 161 to 170, 2003.

Kazumi Arai, et al., "Vaccine efficacy for a novel recombinant baculovirus virion expressing the *Plasmodium berghei* merozoite surface protein 119kDa fragment on its surface", Kokusai Hoken Iryo, 2006 Nen, October, vol. 21, special extra issue, p. 163, Endai Bango P2-05.

Makoto Matsumoto, "Atarashii Vaccine Kaihatsu no Tamerio Zen Rinsho Jikken ni Tsuite, Asia Chiiki tono Kenkyu Network no Katsuyo ni yoru Tazai Taisei Kekkaku no Seigyo ni Kansuru Kenkyu", Heisei 17 Nendo Sokatsu Bntan Kenkyu Hokokusho, 2006 Nen, 3 Gatsu, pp. 112-115.

Abe, Takayuki, et al., "Baculovirus Induces an Innate Immune Response and Confers Protection from Lethal Influenza Virus Infection in Mice", The Journal of Immunology (2003) vol. 171, pp. 1133-1139.

Caton, Andrew J., The Antigenic Structure of the Influenza Virus A/PR/8/34 Hemagglutinin (H1 Subtype), Cell, vol. 31, (1982), pp. 417-427.

European Search Report dated Jul. 22, 2011 issue in corresponding Application No. 1193966.8.

Kaba, Stephen A., "Novel baculovirus-derived p67 subunit vaccines efficacious against East Coast fever in Cattle" Vaccine 23, (2005), pp. 2791-2800.

Mann, Jamie, F.S. et al "Optimisation of a lipid based oral delivery system containing A/Panama influenza haemagglutinin", Vaccine (2004) vol. 22, pp. 2425-2429.

U.S. Office Action dated Jul. 19, 2011 issued in corresponding U.S. Appl. No. 12/192,927.

Safdar, Amar, et al., "Dose-Related Safety and Immunogenicity of Baculovirus-Expressed Trivalent Influenza Vaccine: A Double-Blind, Controlled Trial in Adult Patents with Non-Hodgkin B Cell Lymphona", The Journal of Infectious Diseases, (2006) 194:1394-7.

Tami, Cecilia, et al., "Immunological properties of FMDV-gP64 fusion proteins expressed on SFP cell and baculovirus surfaces" Vaccine, 23, (2004) pp. 840-845.

Office Action issued in corresponding U.S. Appl. No. 13/617,825 on Apr. 1, 2013.

Gardner, Malcolm J., "Genome sequence of the human malaria parasite *Plasmodium falciparum*", Nature (2002), vol. 419, No. 6906, pp. 498-511.

European Search Report dated Jul. 18, 2011 for European Patent Application No. 10193968.4.

\* cited by examiner

Fig. 15

RECOMBINANT BACULOVIRUS VACCINE

TECHNICAL FIELD

The present invention provides a novel transfer vector, a recombinant baculovirus obtained by homologous recombination of the transfer vector and a baculovirus DNA and methods for production thereof.

The present invention also relates to pharmaceuticals (e.g., vaccines, preventive or therapeutic drugs for infectious diseases such as malaria and influenza) comprising the recombinant baculovirus as an active ingredient.

BACKGROUND ART

Baculovirus has been used as a vector for method of industrially producing an objective protein using insect cells. In recent years, it has been found that the baculovirus can introduce a foreign gene not only into the insect cells but also into mammalian cells, and a possibility of the vector in which a gene for therapy is introduced has been found. In Patent document 1, a recombinant baculovirus expression vector having multiple independent promoters composed of a DNA region comprising a gene encoding a viral non-structural protein in the promoter derived from an early gene from the baculovirus and a DNA region comprising a gene encoding a viral structural protein in the promoter derived from a late gene has been disclosed.

In Patent document 2, the method in which a non-mammalian DNA virus comprising a promoter controlled so that an exogenous gene is expressed from a vector in which the desired exogenous genes have been linked to the multiple independent promoters is introduced into a cell and the exogenous gene is expressed in the mammalian cell has been disclosed.

Furthermore, in Patent document 3, the method of producing the protein by gene recombination technology using the baculovirus has been disclosed, and the method of producing the protein by expressing a fusion gene obtained by linking a gp64 gene of the baculovirus to a gene encoding the desired protein, producing the desired protein in a form in which the desired protein has been fused to viral particles, collecting the viral particles fused with the desired protein, and cleaving the desired protein from the viral particles to collect the desired protein has been disclosed.

In Patent document 4, for a baculovirus expression system, a recombinant baculovirus expression vector having multiple independent promoters comprising a first nucleic acid sequence encoding a detection marker linked in the form capable of functioning to a first promoter which is active in a host cell and is inactive in a non-acceptable cell, and a second nucleic acid sequence comprising a foreign nucleic acid sequence linked in the form capable of functioning to a second promoter which is active in the non-acceptable cell has been disclosed.

In patent document 5, it has been disclosed that an influenza virus hemagglutinin (HA) antigen-expressing recombinant baculovirus vector linked to a CAG promoter derived from chicken β actin is useful as a vaccine formulation because the vector has a preventive effect on infection with influenza virus.

In Patent document 6, the method of producing a baculovirus vector comprising a co-transfection step in which a plasmid in which genes encoding proteins expressible on the cell surface have been linked to the baculovirus promoter and the promoter derived from the mammalian cell, respectively, and a plasmid in which genes encoding proteins expressible on the cell surface have been linked to two baculovirus promoters, respectively are co-transfected in the insect cell has been disclosed.

And in patent document 7, a study on an anti-influenza virus activity on the infection with influenza virus using the recombinant baculovirus in which cDNA from influenza virus HA has been incorporated in the CAG promoter has been disclosed, and it has been disclosed that not only the recombinant baculovirus but also a wild type baculovirus has the activity.

This way, in recent years, various recombinant baculoviruses have been developed, and pharmaceutical development for mammals using them has been studied utilizing the recombinant baculovirus as the active ingredient.

In the related art, a recombinant baculovirus vector having a novel structure, and the development of a pharmaceutical formulation, particularly a vaccine formulation using the recombinant baculovirus as the active ingredient, which is effective for infectious diseases such as malaria and influenza, or diseases such as cancer have been desired.

Patent document 1: Japanese Patent No. 3366328, Multiple promoter baculovirus expression system and defect particle products.

Patent document 2: WO98/011243, Non-mammalian DNA virus having modified coating protein.

Patent document 3: JP No. 2002-235236-A, Methods of producing proteins

Patent document 4: JP No. 2003-284557-A, novel baculovirus-transfecting vector and recombinant baculovirus for expression of foreign gene.

Patent document 5: WO02/062381, Baculovirus vector vaccine.

Patent document 6: WO04/029259, Baculovirus vector, method of producing baculovirus vector and method of introducing gene.

Patent document 7: JP No. 2005-15346-A, Baculovirus-containing anti-viral agent.

DISCLOSURE OF INVENTION

Problems to be Solved by the Invention

An object of the present invention is to provide a novel recombinant transfer vector, a recombinant baculovirus obtained by homologous recombination of the recombinant transfer vector and a baculovirus DNA, and methods for production thereof. Another object of the present invention is to provide a pharmaceutical, particularly a vaccine formulation using the recombinant baculovirus as an active ingredient

Means for Solving the Problems

The present inventors have found a transfer vector having a novel structure capable of expressing a protein having a desired immunogenicity, or a fusion protein of a partial protein or the protein having the immunogenicity with cytokine in insect cells and vertebrate (particularly mammal, bird and fish) cells other than insect cells, and a recombinant baculovirus obtained by homologous recombination of the transfer vector and a baculovirus DNA. By providing the recombinant baculovirus, the pharmaceutical having the recombinant baculovirus as the active ingredient having effective preventive and/or therapeutic effects on infectious diseases was extensively studied. As a result, the present inventors have newly found that the recombinant baculovirus has the effect as the desired pharmaceutical.

And, according to the present invention, the recombinant transfer vector having the novel structure, the recombinant baculovirus obtained by homologous recombination of the transfer vector and the baculovirus DNA and the methods for production thereof were confirmed, and it was confirmed that the recombinant baculovirus itself was useful as the pharmaceutical capable of expressing the protein having the desired immunogenicity in the target cells and was useful as the preventive pharmaceutical for the infectious diseases such as malaria and influenza, and here the present invention was completed.

The present invention provides the invention shown in the following [1] to [31]

[1] A method of producing a transfer vector comprising a structure in which dual promoters and a fusion gene have been incorporated, characterized in that the fusion gene comprising at least one gene encoding a protein capable of being a component of a viral particle and at least one immunogenic foreign gene are linked downstream of the dual promoters linking one vertebrate promoter and another baculovirus promoter.

[2] The method according to [1], wherein the vertebrate promoter is a mammalian promoter.

[3] The method according to [1] or [2], characterized in that the gene encoding at least one protein capable of being the component of the viral particle is any of a baculovirus gp64 gene, a Vesicular stomatitis virus glycoprotein gene, a type I human Immunodeficiency virus glycoprotein gene, a human respiratory syncytial virus membrane glycoprotein gene, a type A influenza virus hemagglutinin protein gene, a type B influenza virus hemagglutinin protein gene, a herpes simplex virus glycoprotein gene and a murine hepatitis virus S protein gene.

[4] The method according to [1] or [2], wherein the vertebrate promoter is selected from any of a cytomegalovirus promoter, an SV40 promoter, a retrovirus promoter, a metallothionein promoter, a heat shock protein promoter, a CAG promoter, an elongation factor 1α promoter, an actin promoter, a ubiquitin promoter, an albumin promoter and an MHC class II promoter.

[5] The method according to any of [1] to [4], wherein the baculovirus promoter is selected from a polyhedrin promoter, a p10 promoter, an IE1 promoter, an IE2 promoter, a p35 promoter, a p39 promoter, and a gp64 promoter.

[6] The method according to any of [1] to [5], wherein the immunogenic foreign gene is selected from any of a malaria antigen, an influenza antigen, an *M. tuberculosis* antigen, a SARS virus antigen, a West Nile fever virus antigen, a dengue fever virus antigen, an HIV antigen, an HCV antigen, a *leishmania* antigen, a *trypanosoma* antigen, a leucocytozoon antigen alone, or a fusion antigen of at least one selected from these antigen gene group with a cytokine.

[7] The method according to any of [1] to [6], wherein the transfer vector is any of pDual-Hsp65-gp64, pDual-PbCSP-gp64, pDual-H1N1/HA1-gp64, pDual-PbTRAMP-gp64, pDual-PbAMA1D123-gp64, pDual-PbMSP129-gp64, pDual-PfCSP-gp64, pDual-PfAMA1-gp64, pDual-Pfs25-gp64, pDual-H5N1/HA1-gp64, pDual-SARS/S-gp64, pCP-H1N1/HA1-gp64, pCAP-H1N1/HA1-gp64, pCU-H1N1/HA1-gp64, pDual-H1N1/NP-gp64, pDual-H1N1/M2-gp64, pDual-H1N1/NAe-gp64, pDual-M2e-gp64, pCP-HA1/NC99-gp64, pCP-H1N1/HA0-gp64, pCP-H1N1/HA2-gp64, pCP-H1N1/HA1-vp39 and pCP-H1N1/NP-vp39.

[8] A method of producing a recombinant baculovirus comprising the steps of producing a transfer vector comprising a structure in which dual promoters and a fusion gene have been incorporated, characterized in that the fusion gene comprising at least one gene encoding a protein capable of being a component of a viral particle and at least one immunogenic foreign gene are linked downstream of the dual promoters linking one vertebrate promoter and another baculovirus promoter; co-transfecting the transfer vector and a baculovirus DNA into a host cell of an insect; and separating the recombinant baculovirus.

[9] The method according to [8], characterized in that the gene encoding at least one protein capable of being the component of the viral particle is any of a baculovirus gp64 gene, a Vesicular stomatitis virus glycoprotein gene, a type I human immunodeficiency virus glycoprotein gene, a human respiratory syncytial virus membrane glycoprotein gene, a type A influenza virus hemagglutinin protein gene, a type B influenza virus hemagglutinin protein gene, a herpes simplex virus glycoprotein gene and a murine hepatitis virus S protein gene.

[10] The method according to [9], wherein the vertebrate promoter is selected from any of a cytomegalovirus promoter, an SV40 promoter, a retrovirus promoter, a metallothionein promoter, a heat shock protein promoter, a CAG promoter, an elongation factor 1α promoter, an actin promoter, a ubiquitin promoter, an albumin promoter and an MHC class II promoter.

[11] The method according to any of [8] to [10], wherein the baculovirus promoter is selected from a polyhedrin promoter, a p10 promoter, an IE1 promoter, a p35 promoter, a p39 promoter, and a gp64 promoter.

[12] The method according to any of [8] to [11], wherein the immunogenic foreign gene is selected from any of a malaria antigen, an influenza antigen, an *M. tuberculosis* antigen, a SARS virus antigen, a West Nile fever virus antigen, a dengue fever virus antigen, an HIV antigen, an HCV antigen, a *leishmania* antigen, a *trypanosoma* antigen, a leucocytozoon antigen alone, or a fusion antigen of one selected from these antigen gene group with a cytokine.

[13] The method according to any of [8] to [12], wherein the recombinant baculovirus is any of AcNPV-Dual-Hsp65, AcNPV-Dual-PbCSP, AcNPV-Dual-H1N1/HA1, AcNPV-Dual-PbTRAMP, AcNPV-Dual-PbAMA1D123, AcNPV-Dual-PbMSP129, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39.

[14] A transfer vector comprising a structure in which a fusion gene comprising at least one gene encoding a protein capable of being a component of a viral particle and at least one immunogenic foreign gene were linked downstream of the dual promoters linking one vertebrate promoter and another baculovirus promoter has been incorporated.

[15] The transfer vector according to [14] comprising the structure in which the fusion gene comprising the gene encoding at least one protein capable of being the component of the viral particle and at least one immunogenic foreign gene were linked downstream of the dual promoters linking one vertebrate promoter and another baculovirus promoter has been incorporated.

[16] The transfer vector according to [14] or [15], characterized in that the gene encoding at least one protein capable of being the component of the viral particle is any of a baculovirus gp64 gene, a Vesicular stomatitis virus glycoprotein gene, a type I human immunodeficiency virus glycoprotein gene, a human respiratory syncytial virus membrane glycoprotein gene, a type A influenza virus hemagglutinin protein gene, a type B influenza virus hemagglutinin protein gene, a herpes simplex virus glycoprotein gene and a murine hepatitis virus S protein gene.

[17] The transfer vector according to [15], wherein the vertebrate promoter is selected from any of a cytomegalovirus promoter, an SV40 promoter, a retrovirus promoter, a metallothionein promoter, a heat shock protein promoter, a CAG promoter, an elongation factor 1α promoter, an actin promoter, a ubiquitin promoter, an albumin promoter and an MHC class II promoter.

[18] The transfer vector according to any of [15] to [17], wherein the baculovirus promoter is selected from a polyhedrin promoter, a p10 promoter, an IE1 promoter, an IE2 promoter, a p35 promoter, a p39 promoter, and a gp64 promoter.

[19] The transfer vector according to any of [15] to [18], wherein the immunogenic foreign gene is selected from any of a malaria antigen, an influenza antigen, an *M. tuberculosis* antigen, a SARS virus antigen, a West Nile fever virus antigen, a dengue fever virus antigen, an HIV antigen, an HCV antigen, a *leishmania* antigen, a *trypanosoma* antigen, a leucocytozoon antigen alone, or a fusion antigen of one selected from these antigen gene group with a cytokine.

[20] The transfer vector according to any of [15] to [19] which is any of pDual-Hsp65-gp64, pDual-PbCSP-gp64, pDual-H1N1/HA1-gp64, pDual-PbTRAMP-gp64, pDual-PbAMA1D123-gp64, pDual-PbMSP129, pDual-PfCSP-gp64, pDual-PfAMA1-gp64, pDual-Pfs25-gp64, pDual-H5N1/HA1-gp64, pDual-SARS/S-gp64, pCP-H1N1/HA1-gp64, pCAP-H1N1/HA1-gp64, pCU-H1N1/HA1-gp64, pDual-H1N1/NP-gp64, pDual-H1N1/M2-gp64, pDual-H1N1/NAe-gp64, pDual-M2e-gp64, pCP-HA1/NC99-gp64, pCP-H1N1/HA0-gp64, pCP-H1N1/HA2-gp64, pCP-H1N1/HA1-vp39 and pCP-H1N1/NP-vp39.

[21] A recombinant baculovirus produced by the method of producing the recombinant baculovirus according to any of [8] to [13].

[22] The recombinant baculovirus according to [21] which is any of AcNPV-Dual-Hsp65, AcNPV-Dual-PbCSP, AcNPV-Dual-H1N1/HA1, AcNPV-Dual-PbTRAMP, AcNPV-Dual-PbAMA1D123, AcNPV-Dual-PbMSP129, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39.

[23] A pharmaceutical composition comprising the recombinant baculovirus according to [21] or [22].

[24] The pharmaceutical composition according to [23], comprising any of AcNPV-Dual-H1N1/HA1, AcNPV-H1N1/HA1, AcNPV-CAP-H1N1/HA1, AcNPV-Dual-PfCSP, AcNPV-Dual-PfAMA1, AcNPV-Dual-Pfs25, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39.

[25] A pharmaceutical composition comprising the recombinant baculovirus according to [21] or [22], wherein the composition is administered intramuscularly, intranasally or by inhalation.

[26] A vaccine comprising any of AcNPV-Dual-H1N1/HA1, AcNPV-H1N1/HA1, AcNPV-CAP-H1N1/HA1, AcNPV-Dual-PfCSP, AcNPV-Dual-PfAMA1, AcNPV-Dual-Pfs25, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39 as an active ingredient.

[27] The vaccine according to [26], wherein the vaccine is administered intramuscularly, intranasally or by inhalation.

[28] A therapeutic or preventive agent for influenza virus infection, comprising AcNPV-Dual-H1N1/HA1, AcNPV-H1N1/HA1, AcNPV-CAP-H1N1/HA1, AcNPV-Dual-PfCSP, AcNPV-Dual-PfAMA1, AcNPV-Dual-Pfs25, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39 as an active ingredient.

[29] The therapeutic or preventive agent for influenza virus infection according to [28], wherein the agent is administered intramuscularly, intranasally or by inhalation.

[30] A vaccine for influenza virus infection, comprising any of AcNPV-Dual-H1N1/HA1, AcNPV-H1N1/HA1, AcNPV-CAP-H1N1/HA1, AcNPV-Dual-PfCSP, AcNPV-Dual-PfAMA1, AcNPV-Dual-Pfs25, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39 as an active ingredient.

[31] The vaccine for influenza virus infection according to [30], wherein the agent is administered intramuscularly, intranasally or by inhalation.

EFFECT OF THE INVENTION

According to the present invention, a novel recombinant transfer vector, a recombinant baculovirus obtained by homologous recombination of the recombinant transfer vector and a baculovirus DNA, and methods for production thereof are provided. Pharmaceuticals comprising the recombinant baculovirus of the present invention as the active ingredient are useful as the therapeutic or preventive drugs for the infectious diseases such as malaria, influenza, tuberculosis and hepatitis, cancers and autoimmune diseases, or as cellular medicine and vaccine formulations.

Figure 4:
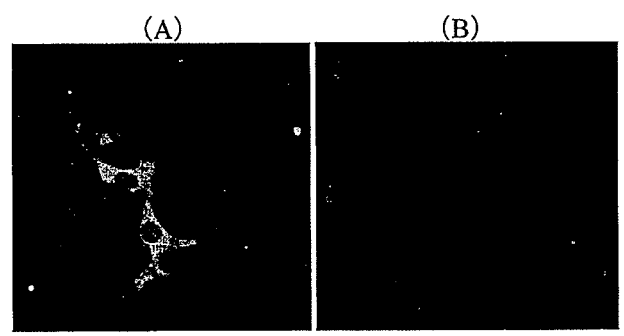

Lane 1: AcNPV-WT
Lane 2: AcNPV-Dual-H1N1/HA1
Lane 3: AcNPV-WT
Lane 4: AcNPV-Dual-Hsp65
Lane 5: AcNPV-WT
Lane 6: AcNPV-Dual-PbCSP;

FIG. 4 is a view of fluorescence labeled staining where recombinant baculovirus produced from recombinant transfer vector in vertebrate cells has expressed a fusion product of tuberculosis HSP65 gene and the gp64 gene.
(A): HepG2 cells transduced with AcNPV-Dual-Hsp65;
(B): HepG2 cells transduced with AcNPV-WT.

Figure 5:
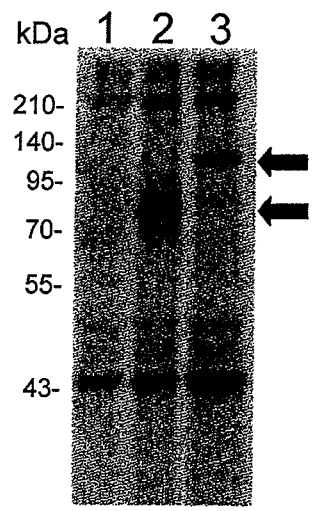

FIG. 5 is a view identifying by immunoprecipitation that the recombinant baculovirus produced from the recombinant transfer vector in the mammalian animal cells has expressed a fusion protein encoded by an influenza virus HA antigen gene and the gp64 gene. Immunoprecipitation of HepG2 cells introduced with recombinant baculoviruses. HepG2 cells were transduced with AcNPV-WT (lane 1), AcNPV-CMV-HA full (lane 2) or AcNPV-Dual-HA1N (lane 3). At 3 h after transduction, cells were radiolabeled with [$^{35}$S]methionine for 12 h. Cell lysates were immunoprecipitated with serum from mice infected with H1N1 influenza virus.

Figure 6:
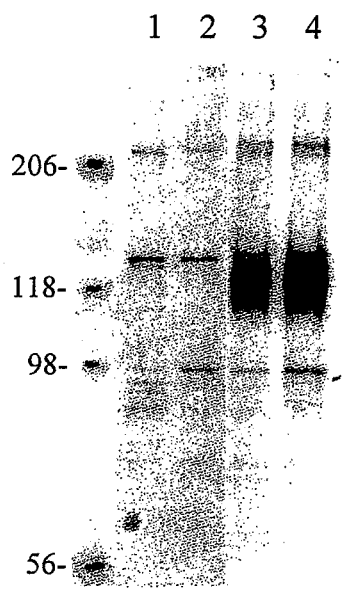

FIG. 6 is a view of Western blotting analysis showing fusion expression of a malaria parasite CSP gene and the gp64 gene in viral particles of the recombinant baculovirus produced from the recombinant transfer vector in insect cells.
Lane 1: AcNPV-WT
Lane 2: AcNPV-CMV-PbCSP
Lane 3: AcNPV-PbCSPsurf
Lane 4: AcNPV-Dual-PbCSP.

Figure 7:
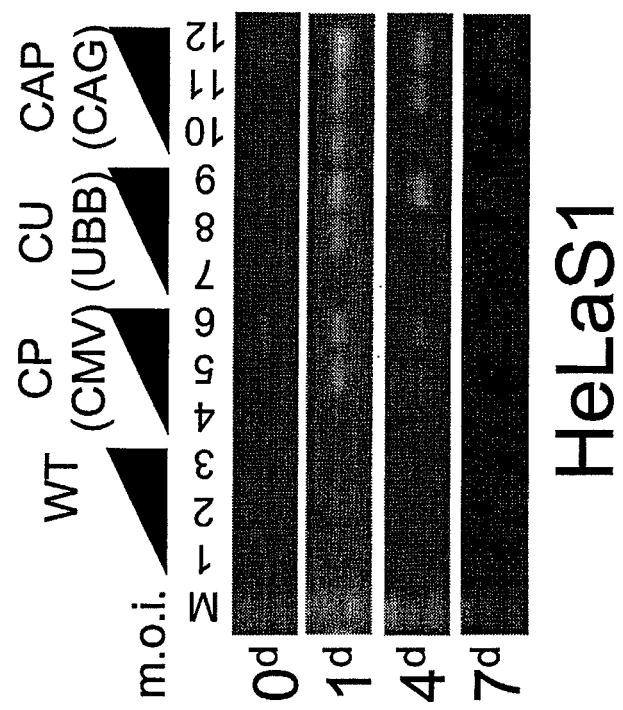

FIG. 7 is a view showing results of RT-PCT identifying that an HA1 antigen recombinant baculovirus obtained by exchanging a vertebrate promoter has expressed a fusion product of HA1 and gp64 in HeLa cells.

Figure 8:
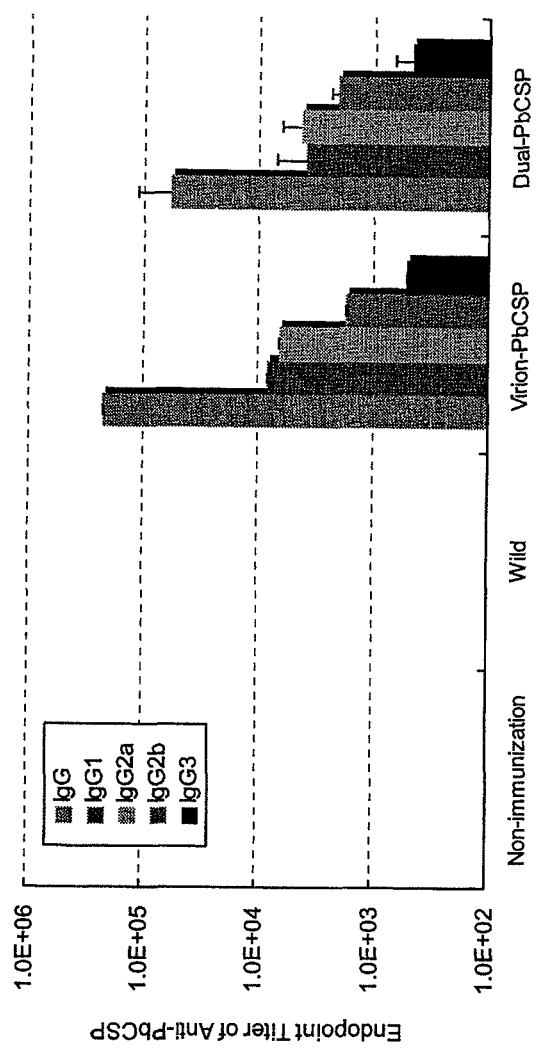

FIG. 8 is a view showing production of IgG antibody specific for a PbCSP antigen in sera from mice inoculated with the recombinant baculovirus.

Figure 9:
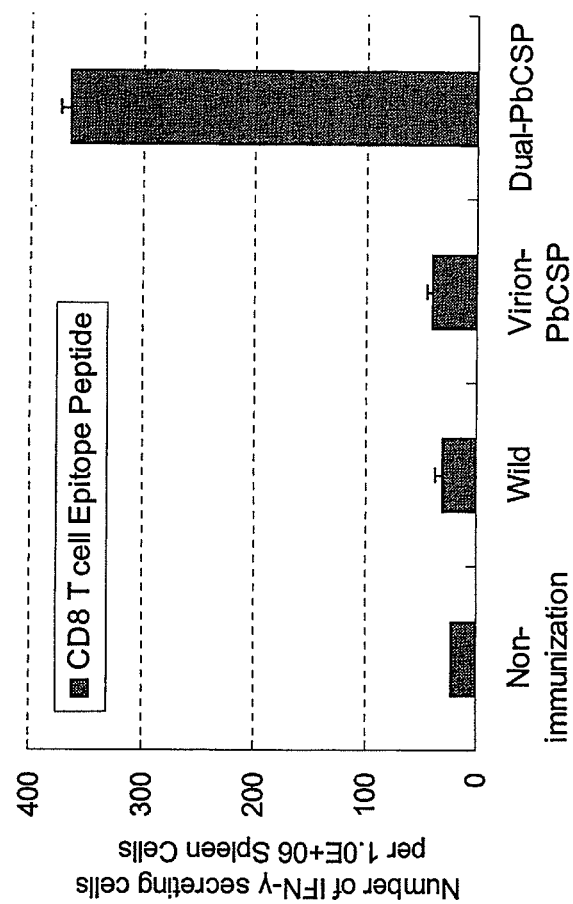

FIG. 9 is a view showing numbers of IFN-γ-producing cells reactive to a CTL epitope of PbCSP in spleen cells from mice inoculated with the recombinant baculovirus.

Figure 10:

FIG. 10 is a view showing preventive effects (virus infectivity titer) by the recombinant baculovirus AcNPV-Dual-M2e on infection with influenza virus.

Figure 11:
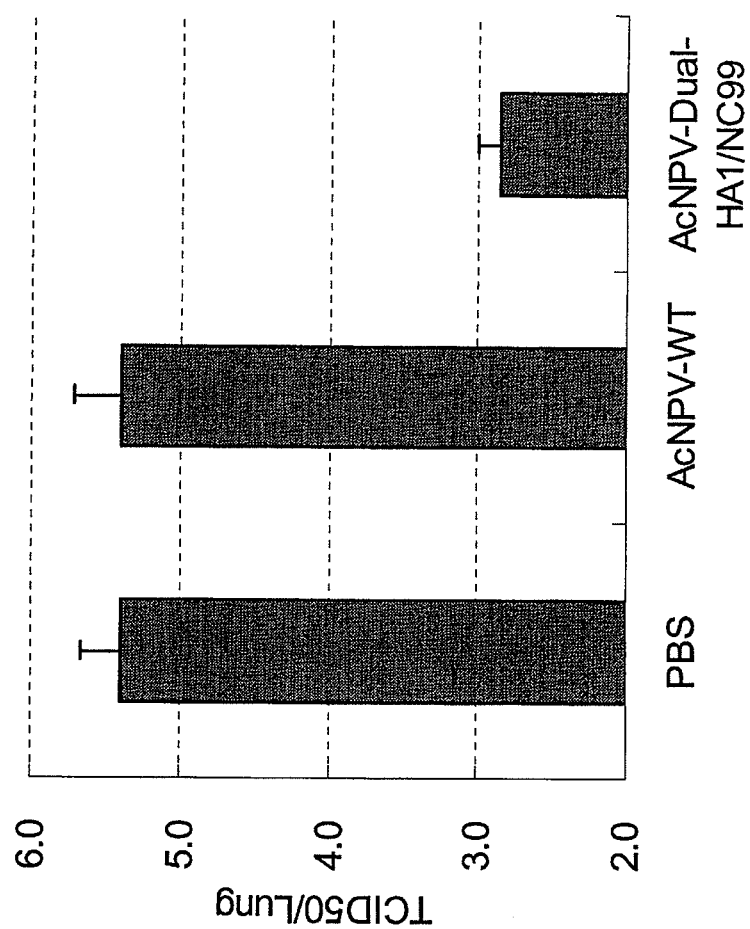

FIG. 11 is a view showing preventive effects (virus infectivity titer) by recombinant baculovirus AcNPV-Dual-HA1/NC99 on infection with influenza virus.

Figure 12:
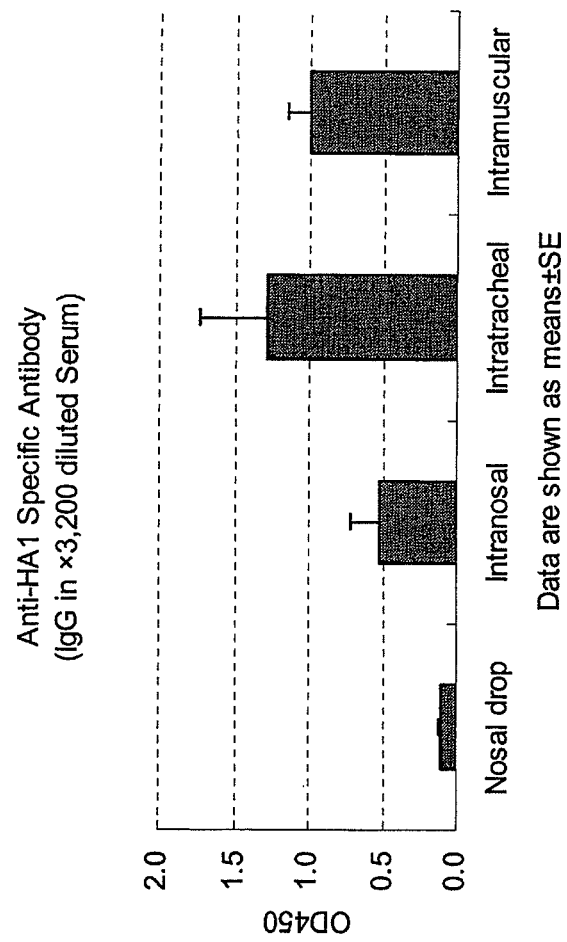

FIG. 12 is a view showing the production of IgG antibody specific for influenza virus in blood, induced by the recombinant baculovirus AcNPV-Dual-H1N1/HA1 administered via different four routes.

Figure 13:
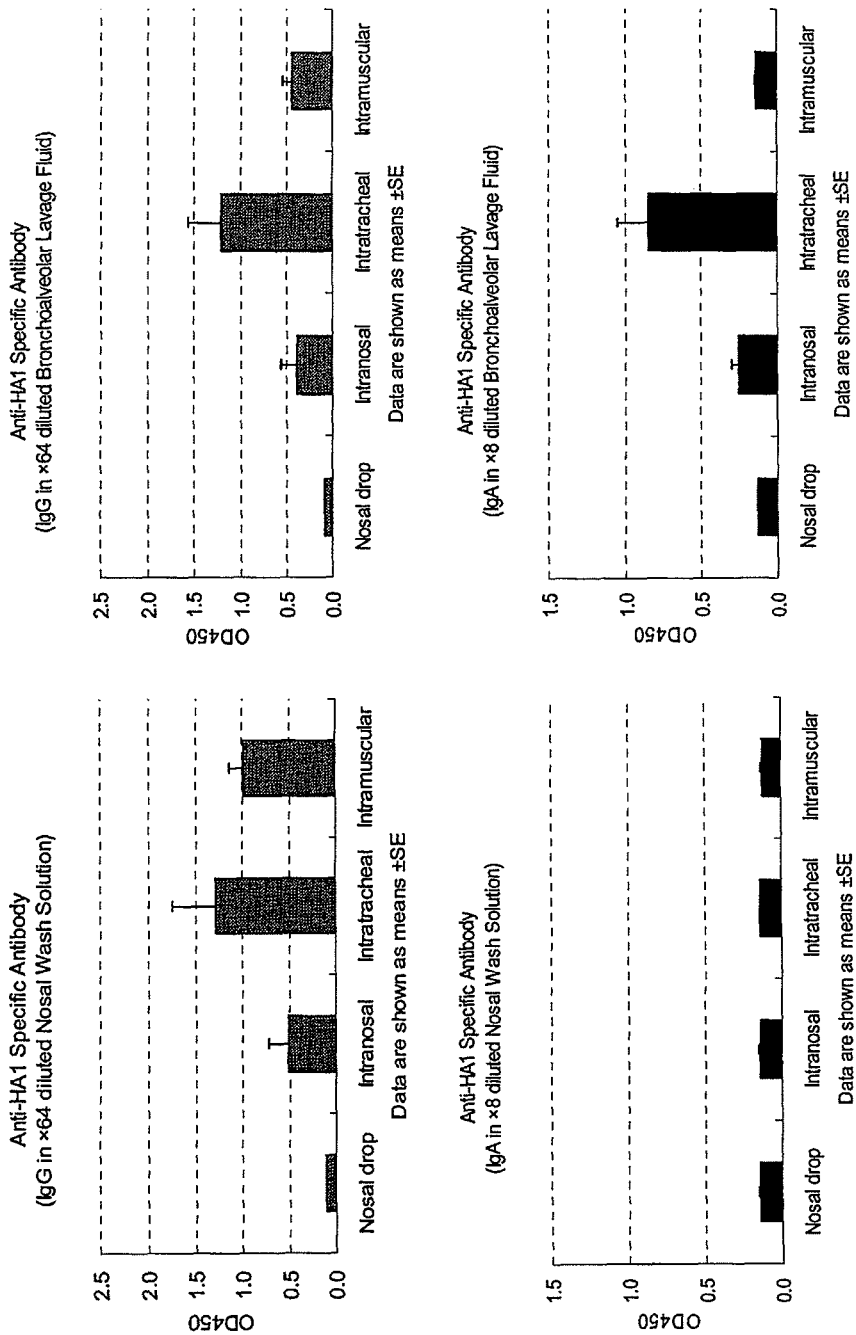

FIG. 13 is a view showing the production of IgG antibody and IgA antibody specific for influenza virus in nasal wash and alveolar wash, induced by the recombinant baculovirus AcNPV-Dual-H1N1/HA1 administered via different four routes.

Figure 14:
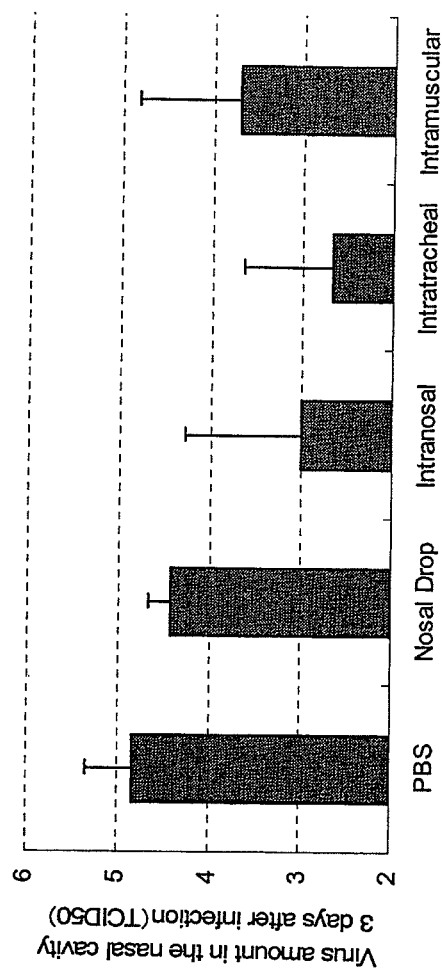

FIG. 14 is a view showing the preventive effects (virus infectivity titer) on influenza virus in nasal cavity by the recombinant baculovirus AcNPV-Dual-H1N1/HA1 administered via different four routes.

Figure 15:
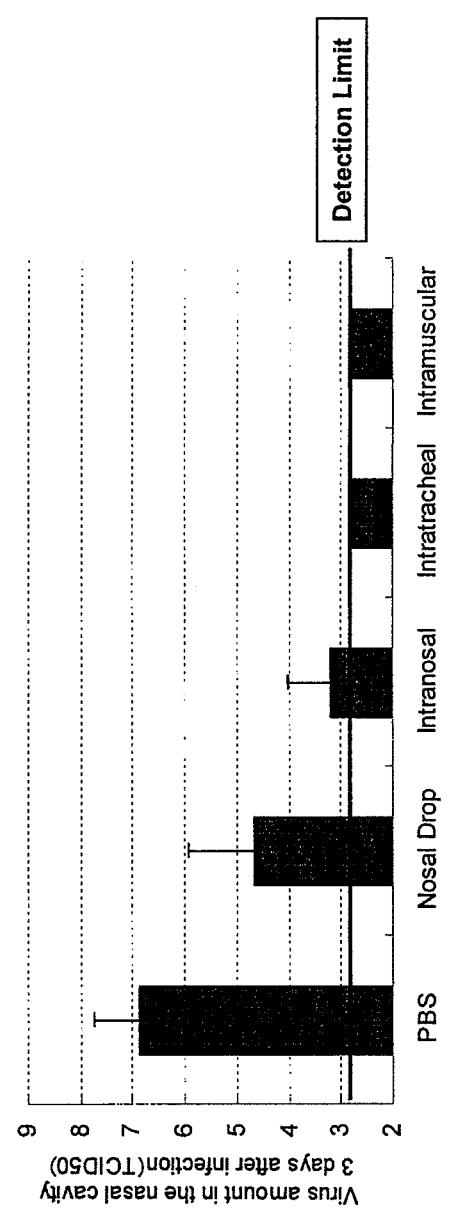

FIG. 15 is a view showing the preventive effects (virus infectivity titer) on intrapulmonary influenza virus by the recombinant baculovirus AcNPV-Dual-H1N1/HA1 administered via different four routes.

BEST MODES FOR CARRYING OUT THE INVENTION

Representation herein by abbreviations of amino acids, peptides, base sequences and nucleic acids accedes to IUPAC-IUB Communication on Biological Nomenclature, Eur. J. Biochem., 138: 9 (1984) defined by IUPAC-IUB, "Guideline for preparing specifications comprising base sequences and amino acid sequences" (Patent Office) and commonly used notes in the art.

A DNA molecule herein encompasses not only double strand DNA but also single strand DNA including sense chains and antisense chains which compose them, and is not limited to a length thereof. Therefore, the polynucleotide (DNA molecule) encoding the immunogenic foreign gene of the present invention includes the double strand DNA including genomic DNA and the single strand DNA (sense chain) including cDNA and the single strand DNA (antisense chain) having the sequence complementary to the sense chain and synthetic DNA fragments thereof unless otherwise mentioned.

The polynucleotide or the DNA molecule herein is not defined by a functional region, and can include at least one of an expression suppression region, a coding region, a leader sequence, an exon and an intron.

The polynucleotide also includes RNA and DNA. The polypeptide composed of the certain amino acid sequence and the polynucleotide composed of the certain DNA sequence include fragments, homologs, derivatives and mutants thereof.

The mutants of the polynucleotide, e.g., mutant DNA include naturally occurring allelic mutants, not naturally occurring mutants and mutants having deletion, substitution, addition and insertion. But, these mutants encode the polypeptide having substantially the same function as the function of the polypeptide encoded by the polynucleotide before the mutation.

In the present invention, the transfer vector refers to a plasmid for producing the recombinant baculovirus, comprising the structure in which a fusion gene linking at least one gene encoding a protein capable of being a component of a viral particle to at least one immunogenic foreign gene has been incorporated downstream of dual promoters linking two promoters which are one vertebrate promoter (mammalian promoter, bird promoter, fish promoter) and another baculovirus promoter.

In one of the preferable embodiment of the invention, it is preferable that the immunogenic foreign gene is located downstream of the dual promoters and upstream of the gene encoding the protein capable of being the component of the viral particle.

The recombinant baculovirus of the present invention is used for vertebrates as the active ingredient of the pharmaceuticals or vaccines. As the vertebrates, mammals including human beings, e.g., horses, swines, sheeps, goats, monkeys, mice, dogs and cats, birds such as chickens, quails, gooses, dabblers, pigeons, turkeys, pintados and parrots, and fishes such as yellow tails, adult yellowtails, sea breams, amberjacks, scads, striped jacks, striped pigfish, salmons, blueback salmons, carps, crucian carps, rainbow trouts, brook trouts and amago trouts can be exemplified.

In one embodiment, the present invention provides the transfer vector comprising the novel structure in which the fusion gene comprising the gene encoding a viral membrane protein expressible in the insect cell and one immunogenic foreign gene has been incorporated under the control of the dual promoters in which one vertebrate promoter has been linked to another baculovirus promoter. By co-transfecting this transfer vector together with the baculovirus DNA into the insect cell to induce the homologous recombination, it is possible to obtain the recombinant baculovirus in which the fusion gene which is under the control of the baculovirus promoter, expresses in the insect cell and can produce a fusion protein capable of being the component of the budded viral particle has been incorporated.

In the present invention, when the recombinant baculovirus is administered to a vertebrate, the fusion protein of the protein capable of being the component of the budded viral particle with the immunogenic protein probably functions as a component vaccine. The recombinant baculovirus administered to the vertebrate invades in the vertebrate cell, a fusion antigen with the objective immunogenic foreign antigen from the viral genome is produced in the vertebrate cell, and functions as a DNA vaccine.

Therefore, in the case of the mammal, by administering the recombinant baculovirus of the present invention to the mammal, the fusion protein of the protein capable of being the component of the viral particle with the immunogenic protein is presented as the antigen, the fusion protein of the protein capable of being the component of the viral particle with the immunogenic protein is produced in the cell of the mammal, and is thought to function as the preventive or therapeutic agent for infections with virus, protozoa and bacteria due to its immunopotential action.

The baculovirus DNA to be co-transfected with the transfer vector may be any of a wild type, a mutant and a recombinant baculovirus DNA. Host cells to be co-transfected include, for example, cells from the insect such as *Spodoptera frugiperda*.

In the present invention, the gene encoding an amino acid sequence of an antigenic protein which is an immunogen of immunotherapy including vaccine therapy for prevention and treatment of infectious diseases such as malaria, influenza and tuberculosis, autoimmune disease and cancers, for example, the gene encoding the amino acid sequence of the protein such as malaria antigen, influenza virus antigen and *M. tuberculosis* antigen is referred to as the immunogenic foreign gene.

Here, the "foreign" gene means the gene introduced from the outside, which corresponds to the "foreign" gene even if the same gene is present in the cell.

In the present invention, the gene encoding the amino acid sequence of the protein which is the above immunogen is not particularly limited as the gene encoding the amino acid sequence of the antigenic protein as long as the gene is the gene encoding the amino acid sequence of the antigenic protein having the immunogenicity against a substance which causes the diseases such as infectious diseases, cancers and autoimmune diseases. Examples of these genes encoding the amino acid sequence of the antigenic protein having the immunogenicity include the followings.

As the gene encoding the amino acid sequence of the malaria antigen, for example, the genes encoding the amino acid sequences of the proteins such as a surface antigen CSP (Circumsporozoite Protein) of sporozoite surface of malaria parasite, MSP1 (merozoite surface protein 1) of a membrane protein of metrozoite surface, a malaria S antigen secreted from erythrocytes infected with malaria, PfEMP1 protein present in knob of the erythrocytes infected with malaria, SERA protein, TRAMP protein and AMA1 protein are exemplified.

As the gene encoding the amino acid sequence of the influenza virus antigen, the genes encoding the amino acid sequences of the proteins such as HA antigen (hemagglutinin antigen), NA antigen (neuraminidase antigen), M2 antigen (matrix protein antigen) and NP antigen (nucleoprotein antigen) can be exemplified.

As the gene encoding the amino acid sequence of the antigenic protein for tuberculosis, the genes encoding the amino acid sequences of the proteins such as HSP65 (65-kDa heat shock protein), α-antigen (Antigen85A, Antigen85B, Antigen85C), Mtb72f, MDP-1, ESAT-6, MPB51m, Mtb8.8, Mtb9.9, Mtb32, Mtb39 and Mtb11.

With respect to vertebrate genes, as the mammalian genes, the genes encoding the amino acid sequences of the antigenic proteins of the infectious diseases in human beings, cattle, horses, swines, sheeps, monkeys, mice, dogs and cats can be exemplified. As the bird genes, the antigen genes (e.g., bird influenza S antigen) of the infectious diseases in chickens, dabblers, pigeons, turkeys, pintados and parrots can be exemplified. As the fish genes, the antigen genes of the infectious diseases in yellow tails, adult yellowtails, sea breams, amberjacks, scads, striped jacks, striped pigfish, salmons, blueback salmons, carps, crucian carps, rainbow trouts, brook trouts and amago trouts are included.

Pathogen genes whose association with the infectious diseases in the above mammals, birds and fishes has been reported are easily available from the institutions where public data such as GenBank registering the pathogen genes have been stored.

In the present invention, for the immunogenic foreign genes, in addition to the above immune antigens present outside the human body, for example, cytokine genes present inside the human body, e.g., an IL-12 gene, an IL-6 gene, an IL-6 receptor gene, an IL-2 gene, an IL-18 gene, an IFN-γ gene and an M-CSF gene, or fusion genes obtained by fusing a given antigen having the immunogenicity with the above antigenic protein using gene recombination technology are also addressed as the immunogenic foreign genes in the present invention as long as they are introduced from the outside.

In the present invention, it is possible to provide the transfer vector having these immunogenic foreign genes and the recombinant baculovirus obtained by homologous recombination thereof, as well as provide a pharmaceutical composition comprising the recombinant baculovirus having the immunogenic foreign gene as the active ingredient and the vaccine formulation composed of the pharmaceutical composition.

The baculovirus used for the present invention is an insect pathogen virus which causes the infection in the insect and is one group (Baculoviridae) of DNA viruses having a cyclic double strand DNA as the gene. Among them, one group of the viruses referred to as a nuclear polyhedorosis virus (NPV) makes an inclusion referred to as a polyhedron in a nucleus in an infected cell in the late phase of the infection. Even if the foreign gene to be expressed is inserted in place of a polyhedron gene, the virus infects, grows and produces the desired foreign gene product in a large amount with no problem. Thus, this has been practically applied to the production of the desired protein in recent years.

As the baculovirus used for the present invention, *Autographa Californica* Nuclear Polyhedorosis Virus: AcNPV, *Bombyx mori* Nuclear Polyhedorosis Virus: BmNPV, *Orgyia pseudotsugata* Nuclear Polyhedorosis Virus: OpNPV and *Lymantria disper* Nuclear Polyhedorosis Virus LdNPV can be exemplified.

The baculovirus DNA may be any DNA which can perform the homologous recombination with the transfer vector of the present invention. Specifically, the viral gene of the baculovirus DNA which can perform the homologous recombination with the transfer vector of the present invention is 130 kbp which is huge, and the immunogenic foreign gene of 15 kbp or more can be inserted. The baculovirus gene itself is scarcely expressed in the vertebrate cells. Thus, there is almost no need to consider its cytotoxicity, and thus, it is thought that no harmful immune response is induced.

(1) Transfer Vector and Production of Transfer Vector of the Present Invention

Production of Immunogenic Foreign Gene DNA

The immunogenic foreign gene DNA capable of being fused to the viral gene, which is one of the components of the baculovirus transfer vector can be easily produced and acquired by synthesizing based on nucleic acid sequence information of the polynucleotide encoding the amino acid sequence of the antigenic protein having the objective immunogenicity disclosed herein, or directly synthesizing (chemical DNA synthesis method) the DNA corresponding to the nucleic acid sequence of a coding region of the immunogenic foreign gene based on the nucleic acid sequence information of the immunogenic foreign gene. General gene engineering techniques can be applied to this production (e.g., see Molecular Cloning 2d Ed, Cold Spring Harbor Lab. Press (1989); Zoku Seikagaku Jikken Kouza, "Idenshi Kenkyuho I, II, III" edited by the Japanese Biochemistry Society, 1986).

As the synthesis methods of the DNA, chemical synthesis means such as phosphate triester method and phosphate amidite method (J. Am. Chem. Soc., 89, 4801 (1967); ibid., 91, 3350 (1969); Science, 150, 178 (1968); Tetrahedron Lett., 22, 1859 (1981); ibid., 24, 245 (1983)) and combination methods thereof can be exemplified. More specifically, the DNA can also be chemically synthesized by a phosphoramidite method or the triester method, and can be synthesized using a commercially available automatic oligonucleotide synthesizer. A double strand fragment can be obtained by synthesizing a complementary chain and annealing the complementary chain with a chemically synthesized single strand under an appropriate condition or adding the complementary chain with appropriate primer sequences to the chemically synthesized single strand using a DNA polymerase.

As specific one aspect of the immunogenic foreign gene DNA produced in the present invention, DNA composed of the DNA sequence encoding the amino acid sequence of the M. tuberculosis antigen protein, the DNA sequence encoding the amino acid sequence of the malaria antigen protein or the DNA sequence encoding the amino acid sequence of the influenza virus antigen protein can be exemplified.

The DNA utilized in the present invention is not limited to the full length DNA sequence of the DNA sequence encoding the amino acid sequence of the polypeptide of the antigenic protein having the immunogenicity, and may be the DNA sequence encoding a partial sequence as long as the protein of the amino acid sequence encoded by the DNA sequence has the immunogenicity.

The DNA utilized in the present invention may be the DNA sequence obtained by fusing the DNA sequence encoding the amino acid sequence of the antigenic protein having the antigenicity to the cytokine gene present inside the human body, e.g., the IL-12 gene, the IL-1 gene, the IL-6 gene, the IL-6 receptor gene, the IL-2 gene, the IL-18 gene, the IFN-α gene, the IFN-β gene, the IFN-γ gene, the TNF gene, the TGF-β gene, the GM-CSF gene and the M-CSF gene.

The fused DNA sequence is not limited to the full length of the coding region of the DNA sequence encoding the amino acid sequence of the polypeptide of the antigenic protein having the antigenicity and the DNA sequence of the cytokine gene, and may be the partial DNA sequence.

The DNA of the immunogenic foreign gene used for the present invention is not limited to the DNA molecule having the such a particular DNA sequence, and can also have the DNA sequence obtained by combining and selecting the optional codon for each amino acid residue. The choice of the codon can be performed in accordance with standard methods. At that time, for example, it is possible to consider a usage frequency of the codon in the host utilized. (Nucleic Acids Res., 9, 43 (1981)).

The method of producing the DNA of the immunogenic foreign gene used for the present invention by gene engineering techniques can be more specifically performed by preparing cDNA library from an appropriate origin which expresses the DNA of the immunogenic foreign gene in accordance with standard methods and selecting the desired clone from the library using an appropriate probe or an antibody against an expressed product which is inherent for the immunogenic foreign gene (see Proc. Natl. Acad. Sci., USA., 78, 6613 (1981); Science, 222, 778 (1983)).

In the above, as the origin of the genomic DNA, various cells, tissues and cultured cells derived therefrom which express the DNA of the immunogenic foreign gene can be exemplified. In particular, it is preferable to use the extract of the erythrocytes infected with malaria parasites, the extract of the cells infected with influenza virus or the extract of M. tuberculosis as the origin. The extraction and separation of total DNA and RNA from the origin, the separation and purification of mRNA and the acquisition and cloning of cDNA can be performed in accordance with the standard methods.

The production of the DNA of the immunogenic foreign gene can also be performed by extracting mRNA of each immunogen, then adding poly A to the RNA, collecting the poly A-added RNA, producing cDNA using a reverse transcriptase, adding restriction enzyme sites to both ends of the cDNA and using a phage library prepared by incorporating the cDNA into the phage, in addition to obtaining using cDNA library of each immunogen obtained by the extraction, separation and purification of mRNA from the immunogenic tissue or cell using the extract as the origin.

The method of screening the DNA of the immunogenic foreign gene from the cDNA library is not particularly limited, and can be performed in accordance with ordinary methods. As the specific method, for example, the method of selecting a corresponding cDNA clone by immunological screening using a specific antibody (e.g., anti-malaria antibody, anti-influenza virus antibody, anti-M. tuberculosis antibody) against the protein produced by the cDNA; a plaque hybridization method using a probe selectively binding to the objective DNA sequence; a colony hybridization method; and the combinations thereof can be exemplified.

As the probe used in the hybridization methods, DNA fragments chemically synthesized based on the information for the DNA sequence of the immunogenic foreign gene are common. The immunogenic foreign gene already acquired and the DNA sequences of fragments thereof can be advantageously utilized as the above probe. Furthermore, a sense primer and an antisense primer designed based on the DNA sequence information of the immunogenic foreign gene can also be used as the probe for the above screening.

The DNA (nucleotides) used as the probe is the partial DNA (nucleotides) corresponding to the DNA sequence of the immunogenic foreign gene, and one having at least 15 consecutive DNA, preferably at least 20 consecutive DNA and more preferably at least 30 consecutive DNA. A positive clone itself for producing the above DNA can also be used as the probe.

When the DNA of the immunogenic foreign gene is acquired, a DNA/RNA amplification method by PCR (Science, 230, 1350 (1985)) can be utilized suitably. In particular, when a full length cDNA is hardly obtained from the library, RACE method [Rapid amplification of cDNA ends; Jikken Igaku 12(6), 35 (1994)], in particular, 5'-RACE method [M. A. Frohman, et al., Proc. Natl. Acad. Sci., USA., 8, 8998 (1988)] is suitably employed.

The primer used for the PCR can be designed based on the DNA sequence information of the immunogenic foreign gene, and synthesized in accordance with the standard methods. As this primer, as shown in Examples described later, DNA portions (SP6 promoter primer and T7 terminator primer) added to both ends of the vector plasmid in which the DNA of the immunogenic foreign gene has been incorporated in can also be used.

The isolation/purification of the DNA/RNA fragment amplified by PCR can be performed in accordance with the standard methods, e.g., gel electrophoresis.

For the DNA of the immunogenic foreign gene obtained as the above or various DNA fragments, their DNA sequences can be determined in accordance with the standard methods, e.g., dideoxy method (Proc. Natl. Acad. Sci., USA., 74, 5463 (1977)) or Maxam-Gilbert method (Methods in Enzymology, 65, 499 (1980)), or simply using a commercially available sequencing kit.

The gene encoding the amino acids of the protein capable of being the component of the viral particle may be any one as long as it is the gene encoding the protein expressible as the protein capable of being the component of the viral particle in the insect cell and as the fusion protein by fusing the immunogenic foreign gene in the objective cell.

As the gene encoding the amino acids of the protein capable of being the component of the viral particle, for example, the genes of a gp64 protein (GenBank Accession No. L22858), a Vesicular stomatitis virus glycoprotein (GenBank Accession No. M21416), a herpes simplex virus glycoprotein (KOS; GenBank Accession No. K01760), a type I human immunodeficiency virus gp120 (GenBank Accession No. U47783), a human respiratory syncytial virus membrane glycoprotein (GenBank Accession No. M86651), a type A influenza virus hemagglutinin protein (GenBank Accession No. U38242), or the gene of envelop proteins of viruses closely related to the baculovirus can be exemplified. In the present invention, the gp64 gene shown in Examples described later can be preferably exemplified.

The DNA of the gene encoding the amino acids of the protein capable of being the component of the viral particle can be easily produced and acquired by synthesizing based on the nucleic acid sequence information of the polynucleotide encoding the amino acid sequence of the polypeptide of the gene encoding the amino acids of the objective protein capable of being the component of the viral particle, or by directly synthesizing the DNA corresponding to the nucleotide sequence encoding the amino acid sequence based on the amino acid sequence information of the gene encoding the amino acids of the protein capable of being the component of the viral particle (chemical DNA synthesis) as is the case with the production of the DNA of the immunogenic foreign gene.

A DNA sequence corresponding to a nucleic acid sequence encoding amino acids of a protein capable of being a component of a viral particle is not limited to a full length of a coding region, and may be DNA composed of a partial DNA sequence.

As is the case with the production of the DNA molecule of the immunogenic foreign gene, the DNA of the gene encoding the amino acids of the protein capable of being the component of the viral particle can be produced by general gene engineering techniques (e.g., see Molecular Cloning 2d Ed, Cold Spring Harbor Lab. Press (1989); Zoku Seikagaku Jikken Kouza, "Idenshi Kenkyuho I, II, III" edited by the Japanese Biochemistry Society, 1986).

In the present invention, the commercially available vector plasmid in which a part of the promoter which controls the expression of the immunogenic foreign gene described later has been already incorporated and the gene (portion) encoding the amino acids of the protein capable of being the component of the viral particle has been previously introduced can also be used.

Vertebrate Promoters

As the vertebrate promoter (capable of functioning in vertebrates) which is one of the components of the transfer vector used for the present invention, the promoters such as mammalian promoters, bird promoters and fish promoters can be exemplified.

Mammalian Promoters

As the mammalian promoter (capable of functioning in mammals) which is one of the components of the transfer vector used for the present invention, a cytomegalovirus promoter, an SV40 promoter, a retrovirus promoter, a metallothionein promoter, a heat shock protein promoter, a CAG promoter, an elongation factor 1α promoter, an actin promoter, a ubiquitin promoter, an albumin promoter and an MHC class II promoter can be exemplified.

Bird Promoters

As the bird promoters, the actin promoter, the heat shock protein promoter, the elongation factor promoter, the ubiquitin promoter and the albumin promoter can be exemplified.

Fish Promoters

As the fish promoters, the actin promoter, the heat shock protein promoter and the elongation factor promoter can be exemplified.

Baculovirus Promoters

As the baculovirus promoter which is one of the components of the baculovirus transfer vector used for the present invention, a polyhedrin promoter, a p10 promoter, an IE1 promoter, a p35 promoter, a p39 promoter, and a gp64 promoter can be exemplified.

Production of Recombinant Transfer Vector

The present invention relates to the novel transfer vector having the structure capable of expressing the objective immunogenic foreign gene as the antigenic protein in both the insect cell and the vertebrate cell, particularly the mammalian cell. In the present invention, the structure of the novel transfer vector produced is characterized in that the DNA sequence encoding the amino acid sequence of the desired Immunogenic protein and the DNA sequence encoding the amino acid sequence of the protein capable of being the component of the viral particle are linked downstream of the linked promoters which are one vertebrate promoter, particularly the mammalian promoter and another baculovirus promoter. DNA regions comprising the DNA sequences of two promoter which are one vertebrate promoter, particularly the mammalian promoter and another baculovirus promoter may be directly linked, or an intervening DNA sequence may be present between the DNA sequences of the two promoters (but, in this case, respective promoters are necessary to have the activity in the insect cell and the vertebrate cell, particularly mammalian cell). Either the vertebrate promoter, particularly the mammalian promoter or the baculovirus promoter to be linked may be disposed more closely to the gene to be expressed in their promoter region. In Examples described later, the baculovirus is disposed more closely to the gene to be expressed than the mammalian promoter.

In the structure, for the fusion gene comprising the gene encoding the protein capable of being the component of the viral particle and the desired immunogenic foreign gene, these two genes may be directly lined, or the intervening DNA sequence may be present between them (but, it is necessary to dispose the DNA to cause no frameshift). It is preferable that an antigen presenting region of the protein encoded by the foreign gene having the desired immunogenicity is fused to the protein capable of being the component of the viral particle. Thus, it is necessary to use in the form fused without cutting off the protein encoded by the foreign gene having the desired immunogenicity from the protein capable of being the component of the viral particle.

A fusion gene comprising these two genes may be formed in advance and this may be incorporated in the vector. Alternatively, any one gene may be incorporated in the vector in advance, and subsequently the other gene may be incorporated in the vector to form the fusion gene in the vector.

For the above manipulations, commercially available expression vectors already having the promoter regions of the above vertebrate promoter, particularly the mammalian promoter and baculovirus promoter and the gene regions encoding the amino acid sequence capable of being the component of the viral particle, which are portions of the constitution required as the transfer vector of the present invention may be used. Utilizing them, the required components may be inserted by inserting the DNA sequence in which the desired immunogenic foreign gene has been fused to the gene encoding the amino acid sequence of the protein capable of being the component of the viral particle in the cloning region of the vector by optionally cutting off with restriction enzymes or incorporating into another vector, or inserting the desired immunogenic foreign gene into the N terminus side of the DNA region of the gene encoding the amino acid sequence of the protein capable of being the component of the viral particle already incorporated in the plasmid.

For the detection of the protein, a His-tag or an HVS-tag may be added before a poly A tail at a C terminus side of the DNA sequence fusing the desired immunogenic foreign gene to the gene encoding the amino acid sequence of the protein capable of being the component of the viral particle. Alternatively, for the expression, the purification and the detection of the recombinant fusion protein, the DNA sequence encoding a FLAG sequence composed of 8 amino acids may be inserted as a peptide tag between the promoter region and the region in which the desired immunogenic foreign gene has been fused to the gene encoding the amino acid sequence of the protein capable of being the component of the viral particle. In the present invention, the plasmid vector having the structure capable of expressing the desired immunogenic foreign protein as the antigenic protein in both the insect cell and the vertebrate cell, particularly the mammalian cell may be produced by using the commercially available plasmid having the structure already satisfying the portion thereof. The amino acid sequence of the peptide may intervene for cleaving the fusion protein with the enzyme in the vertebrate cell. In the transfer vector of the present invention, an enhancer for increasing a transcription activity in the vertebrate cell, particularly the mammalian cell may be disposed upstream of the two promoters, or the DNA sequence encoding the amino acid sequence of a signal peptide for facilitating extracellular secretion of the expressed protein in the host may be bound to the gene to be fused and expressed. A vertebrate terminator region, e.g., a rabbit β globulin terminator which is effective in the vertebrate cell may be disposed for terminating the transcription downstream the gene to be fused and expressed.

As the above, the transfer vector capable of expressing the fusion gene of the immunogenic foreign gene capable of expressing the desired immunogenicity in the baculovirus particle and the gene encoding the amino acid sequence of the protein capable of being the component of the viral particle can be produced.

For specific examples of the transfer vector and the method for production thereof, as shown in Examples described later, the transfer vector composed of the structure in which the cytomegalovirus (CMV) promoter, the CAG promoter modified from CMV promoter, and the ubiquitin (UBB) promoter fused CMV enhancer as the vertebrate promoter, particularly the mammalian promoter and the polyhedrin (Polh) promoter as the baculovirus promoter have been linked and the DNA sequence in which the influenza virus antigen gene, the malaria antigen gene and the *M. tuberculosis* antigen gene as the foreign genes and the gp64 antigen gene as the gene encoding the amino acid sequence of the protein capable of the component of the viral particle were fused has been incorporated can be exemplified as pDual-Hsp65-gp64, pDual-PbCSP-gp64, pDual-H1N1/HA1-gp64, pDual-PbTRAMP-gp64, pDual-PbAMA1D123-gp64, pDual-PbMSP129-gp64, pDual-PfCSP-gp64, pDual-PfAMA1-gp64, pDual-Pfs25-gp64, pDual-H5N1/HA1-gp64 and pDual-SARS/S-gp64, pCP-H1N1/HA1-gp64, pCAP-H1N1/HA1-gp64, pCU-H1N1/HA1-gp64, pDual-H1N1/NP-gp64, pDual-H1N1/M2-gp64, pDual-H1N1/NAe-gp64, pDual-M2e-gp64, pCP-HA1/NC99-gp64, pCP-H1N1/HA0-gp64, pCP-H1N1/HA2-gp64, pCP-H1N1/HA1-vp39, pCP-H1N1/NP-vp39.

(2) Production of Recombinant Baculovirus

The present invention provides the method of producing the recombinant baculovirus comprising the steps of producing the transfer vector composed of the structure in which fusion gene comprising at least one gene encoding the protein capable of being the component of the viral particle and at least one immunogenic foreign gene linked downstream of the dual promoters linking one vertebrate promoter and another baculovirus promoter has been incorporated, co-transfecting the transfer vector and the baculovirus DNA into the host cell and separating the recombinant baculovirus.

In the above method of producing the recombinant baculovirus, the methods of introducing the desired recombinant DNA (transfer vector) into the host and the methods of transforming therewith are not particularly limited, various methods which are well known and commonly used can be employed, and for example, can be performed in accordance with the ordinary gene recombination technology (e.g., Science, 224, 1431 (1984); Biochem. Biophys. Res. Comm., 130, 692 (1985); Proc. Natl. Acad. Sci. USA, 80, 5990 (1983). The recombinant DNA (transfer vector) can be expressed and produced with reference to Ohno et al., "Tanpaku Jikken Protocol 1 Functional analysis, Saibo Kogaku Bessatu Jikken Protocol Series, 1997, Shujunsha". For general techniques of handling of the insect cells, gene recombination and co-transfection, the same techniques as in the well-known methods of making recombinant virus in insect cells can be used (Zenji Matsuura, Proteins, Nucleic acids and Enzymes, 37:211-222, 1992; Zenji Matsuura, Saibo 33(2):30-34, 2001).

The resulting recombinant baculovirus can be cultured in accordance with the standard methods. By the culture, a fusion product (expressed product) in which the DNA of the immunogenic foreign gene and the DNA encoding the amino acid sequence of the protein capable of being the component of the viral particle of the present invention have been fused designed as desired is expressed, produced (accumulated) and secreted inside, outside the cells or on the cell membrane.

As a medium used for the culture, various media commonly used can be appropriately selected and used depending on the host cells employed, and the culture can be performed under the condition suitable for growth of the host cells.

The method of producing the recombinant baculovirus more particularly comprises the steps of preparing the baculovirus DNA for performing the homologous recombination with the transfer vector produced above and co-transfecting the transfer vector and the baculovirus DNA in the insect cells such as Sf-9 cells, Sf-21 cells derived from *Spodoptera frugiperda*, Tn5 cells (High Five cells supplied from Invitrogen) derived from *Trichoplusia ni* as the host cells.

The baculovirus DNA produced above for performing the homologous recombination with the transfer vector may be any of the wild type, the mutant or the recombinant baculovirus DNA.

A baculovirus DNA can enhance a probability of homologous recombination as long as it has the DNA structure homologous to the DNA derived from the baculovirus DNA located upstream of the dual promoters used for the transfer vector so as to produce the homologous recombination with the transfer vector of the present invention, except for the DNA derived from a baculovirus which sandwichs a fusion gene in which DNA in the dual promoter region, the immunogenic foreign gene and the gene encoding the protein capable of being the component of the viral particle have been fused.

To induce the homologous recombination, it is better that the transfer vector and the baculovirus DNA is mixed at a weight ratio of about 1:1 to 10:1.

After introducing into the insect cell simultaneously by the step of co-transfection and culturing the cell, plaques of the virus are made from the culture supernatant, then suspended in the medium, subsequently the virus is eluted from the agar by vortex to yield a solution comprising the recombinant virus.

In the above, the commercially available baculovirus DNA may be used, and for example, it is possible to use BacVector-1000 DNA and BacVector-2000 DNA (supplied from Novagen) in which the polyhedrin gene has been removed from AcNPV.

The co-transfection of the transfer vector and the baculovirus DNA obtained above into the insect cell for the homologous recombination can be performed using the commercially available vector transfection kit described above (BacVector Transfection Kits supplied from Novagen) in accordance with instructions attached to the vector transfection kit. As the above, the transfer vector produced above can be co-transfected together with the baculovirus DNA in the insect cell such as Sf-9 cell to yield the recombinant baculovirus.

In the present invention, in accordance with the above method of producing the recombinant baculovirus, the transfer vectors such as pDual-Hsp65-gp64, pDual-PbCSP-gp64, pDual-H1N1/HA1-gp64, pDual-PbTRAMP-gp64, pDual-PbAMA1D123-gp64, pDual-PbMSP129-gp64, pDual-PfCSP-gp64, pDual-PfAMA1-gp64, pDual-Pfs25-gp64, pDual-H5N1/HA1-gp64, pDual-SARS/S-gp64, pCP-H1N1/HA1-gp64, pCAP-H1N1/HA1-gp64, pCU-H1N1/HA1-gp64, pDual-H1N1/NP-gp64, pDual-H1N1/M2-gp64, pDual-H1N1/NAe-gp64, pDual-M2e-gp64, pCP-HA1/NC99-gp64, pCP-H1N1/HA0-gp64, pCP-H1N1/HA2-gp64, pCP-H1N1/HA1-vp39, pCP-H1N1/NP-vp39, and the baculovirus DNA were used and co-transfected in the Sf-9 insect cell to yield the recombinant baculoviruses such as AcNPV-Dual-Hsp65, AcNPV-Dual-PbCSP, AcNPV-Dual-H1N1/HA1, AcNPV-Dual-PbTRAMP, AcNPV-Dual-PbAMA1D123, AcNPV-Dual-PbMSP129, AcNPV-Dual-PfCSP, AcNPV-Dual-PfAMA1, AcNPV-Dual-Pfs25, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39.

Also, the recombinant baculoviruses such as AcNPV-Dual-H5N1/HA1 and AcNPV-Dual-SARS/S can be obtained.

In addition to the above method of producing the recombinant baculovirus, as the other method of producing the recombinant baculovirus, it is possible to use the method of inserting the foreign gene efficiently in *Escherichia coli* by utilizing a transposon for a phagemid (bacmid) in which the entire baculovirus genome has been incorporated. According to the method, the recombinant baculovirus can be easily produced and collected by only extracting the bacmid bearing the viral gene from microbial cells and transfecting it in the insect cell.

The purification of the recombinant baculovirus of the present invention obtained by the above method of producing the recombinant baculovirus can be performed using the virus purification method known publicly.

For the purification of the recombinant baculovirus, for example, 0.5 to 1.0 mL of a stock virus (usually $1 \times 10^{7-8}$ pfu/mL) obtained by the above method of producing the recombinant baculovirus is inoculated to the insect cells ($1 \times 10^7$ cells/10 cm dish) such as Sf-9 cells, the culture supernatant is collected several days (4 days) after the infection, and a virus pellet obtained by centrifugation is suspended in buffer such as PBS. The resulting suspension is applied on sucrose gradient of 10 to 60%, which is then centrifuged (25,000 rpm, 60 minutes, 4° C.) to collect a virus band. The collected virus is further suspended in PBS, subsequently centrifuged (same condition as the above), and the resulting purified recombinant virus pellet is stored in the buffer such as PBS at 4° C.

An infectivity titer of the above resulting purified recombinant virus can be measured by plaque assay (Fields VIROLOGY 4th Edition p29-32 2001) using the insect cells such as Sf-9 cells.

In the recombinant virus exemplified in the present invention, the N terminus of the baculovirus protein gp64 is exposed outside the particle and its C terminus is exposed inside the particle. Thus, if the protein encoded by the desired immunogenic foreign gene is fused to the N terminus of gp64, the entity thereof as the component of the viral particle is exposed outside the viral protein particle in the insect cell, and thus the antigen is more easily presented, which is suitable for the object of the vaccine formulation of the present invention.

(3) Pharmaceutical Composition of the Present Invention (Pharmaceutical Comprising Recombinant Baculovirus of the Present Invention as Active Ingredient)

The recombinant baculovirus of the present invention which is the active ingredient in the pharmaceutical composition of the present invention can be obtained by the gene engineering techniques shown in the above (2).

It is important for the pharmaceutical composition of the present invention to contain as the active ingredient the recombinant baculovirus obtained by homologous recombination of the baculovirus DNA and the transfer vector constructed so that the fusion gene fusing the immunogenic foreign gene of the present invention to the gene encoding the amino acid sequence of the protein capable of being the component of the viral particle can be expressed in the insect cells and the vertebrate cells, particularly cells from mammals including human being.

In particular, the present invention provides the pharmaceutical composition comprising any of the particular recombinant baculovirus, such as AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 or AcNPV-CP-H1N1/NP-vp39 as the active ingredient.

The recombinant baculovirus of the present invention, such as AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39, which is the active ingredient in the pharmaceutical composition of the present invention has the actions which enhances an infection-preventing effect on the infectious antigen and reduces the infectivity titer, and this action or activity can be utilized for procedures of the diseases associated with the infection of the target cells or tissues. Such target cells affected by the infection include, for example blood cells, and other target cells include hepatic cells, renal cells, brain cells, lung cells, epithelial cells and muscular cells. The tissues comprising these cells include lung, liver, kidney, arterial and venous veins, stomach, intestine, urethra, skin and muscle.

The pharmaceutical composition enhances the infection-preventing effect on infectious antigens such as malaria antigens, e.g., the surface antigen CSP of sporozoite surface of malaria parasite, the MSP1 of the membrane protein of metrozoite surface, the malaria S antigen secreted from erythrocytes infected with malaria, the PfEMP1 protein present in knob of the erythrocytes infected with malaria, the SERA protein, the TRAMP protein and the AMA1 protein as well as influenza antigens e.g., the HA antigen, the NA antigen, the M2 antigen and the NP antigen, and reduces the infectivity titer (e.g., viral infectivity titer). Thus, a surviving period and a survival rate of the mammals including human beings administered with the pharmaceutical composition of the present invention are increased compared with those not administered. Therefore, the pharmaceutical composition of the present invention is useful as the preventive or therapeutic agent for infection with particularly malaria and influenza virus.

The pharmaceutical composition of the present invention is useful as the preventive or therapeutic agent for infectious diseases caused by the pathogen and their complications, e.g., viral diseases caused by influenza virus, papilloma virus, herpes virus, AIDS virus, hepatitis C virus, SARS virus, west Nile fiver virus and dengue fever virus, parasite diseases caused by malaria, trypanosome and *leishmania* parasites, and bacterial diseases caused by bacteria, such as dysentery, enteric fever, cholera, pneumococcus, MRSA, VRE, *Neisseria gonorrhoeae* and *Chlamydia*, syphilis and tuberculosis by utilizing the actions to enhance the infection-preventing effect on the infectious antigen and reduce the infectivity titer.

By using the immunogenic foreign gene for the vertebrate other than the human being in the transfer vector for obtaining the recombinant baculovirus which is the active ingredient in the pharmaceutical composition of the present invention, it is possible to utilize the pharmaceutical composition of the present invention for procedures of the diseases associated with the infection of the target cells and the tissue as chicken influenza vaccine, bovine trypanosome vaccine and Japanese trout cold water disease vaccine by utilizing its actions to enhance the infection-preventing effect on the infectious antigen and reduce the infectivity titer.

The pharmaceutical composition of the present invention can be prepared as the composition comprising the pharmaceutically effective amount of the recombinant baculovirus and a pharmaceutically acceptable carrier.

For the infection-preventing effect of the recombinant baculovirus of the present invention in the vertebrate, particularly, the mammals including the human being or the mammalian cells, for example, the pharmaceutical composition produced by the recombinant baculovirus of the present invention and the composition capable of being added for pharmaceutical administration is administered intramuscularly, intranasally or by inhalation in the vertebrate, particularly, the mammal including the human being, which is subsequently immunized with the pharmaceutical composition comprising the recombinant baculovirus of the present invention as the active ingredient multiple times. The pharmaceutical composition of the invention is administered particularly by inhalation.

And, the preventive effect on the infection can be evaluated by after immunizing with the pharmaceutical composition of the present invention multiple times, administering the pathogen to be subjected to the vertebrate, particularly, the mammal including the human being, and after passing a certain period, comparing the survival rate of the vertebrates, particularly, the mammals including the human beings administered with the recombinant baculovirus which is the active ingredient in the pharmaceutical composition of the present invention with those not administered therewith.

(4) Vaccine of the Present Invention

The recombinant baculovirus, such as AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 or AcNPV-CP-H1N1/NP-vp39 which is the active ingredient of the pharmaceutical composition of the present invention is purified as the viral particle budded from the insect cell, comprising an expressed product of the fusion DNA sequence fusing the gene encoding the amino acid sequence of the protein capable of being the component of the viral particle to the immunogenic foreign gene of the present invention having the desired immunogenicity to enhance the preventive effect on the infection with the pathogen and exhibit the action to reduce the infectivity titer. Then, it is thought that the foreign antigen protein which became the component of the viral particle facilitates acquired immunity (humoral immunity and cellular immunity) by administering the pharmaceutical composition in the form of the viral particle to the vertebrate, particularly, the mammals including the human being, and further the antigenic protein which is the expressed product of the fusion DNA sequence further facilitates the acquired immunity (humoral immunity and cellular immunity) in the vertebrate cells, particularly, the cells in the mammals including the human being. Thus, the recombinant baculovirus of the present invention is useful as the vaccine.

In particular, the present invention provides the vaccine comprising any of the particular recombinant baculovirus such as AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39 as the active ingredient.

As is the case with the pharmaceutical composition of the above (3), the vaccine enhances the preventive effect on the infection and reduces the infectivity titer (e.g., viral infectivity titer) for pathogenic organisms such as malaria antigens e.g., the surface antigen (CSP) of sporozoite surface of malaria parasite, the MSP1 of a membrane protein of metrozoite surface, the malaria S antigen secreted from erythrocytes infected with malaria, the PfEMP1 protein present in knob of the erythrocytes infected with malaria, the SERA protein, the TRAMP protein and the AMA1 protein or the influenza virus HA antigen, the influenza virus NA antigen, the influenza virus M2 antigen and the influenza virus NP antigen. Thus, by comparing the surviving period and the survival rate in the infected mammals including human beings with those not administered with the pharmaceutical composition of the present invention, the vaccine is particularly useful as the preventive or therapeutic agent for the infection with malaria and influenza virus.

The vaccine of the present invention is useful as the preventive or therapeutic agent for infectious diseases caused by the pathogen and their complications, e.g., the viral diseases caused by influenza virus, papilloma virus, herpes virus, AIDS virus, hepatitis C virus, SARS virus, west Nile fiver virus and dengue fever virus, the parasite diseases caused by malaria, trypanosome and *leishmania* parasites, and bacterial diseases caused by bacteria of dysentery, enteric fever, cholera, pneumococcus, MRSA, VRE, *Neisseria gonorrhoeae* and *Chlamydia*, syphilis and tuberculosis, by utilizing the actions to enhance the infection-preventing effect on the infectious antigen and reduce the infectivity titer.

By using the immunogenic foreign gene for the vertebrate other than the human being in the transfer vector for obtaining the recombinant baculovirus which is the active ingredient in the vaccine of the present invention, it is possible to utilize the pharmaceutical composition of the present invention for procedures of the diseases associated with the infection of the target cells and the tissue as chicken influenza vaccine, bovine trypanosome vaccine and Japanese trout cold water disease vaccine by utilizing its actions to enhance the infection-preventing effect on the infectious antigen and reduce the infectivity titer.

The recombinant baculovirus, such as AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39 of the present invention, which is the active ingredient in the vaccine of the present invention has the actions which enhances an infection-preventing effect on the infectious antigen and reduces the infectivity titer, and this action or activity can be utilized for procedures of the diseases associated with the infection of the target cells or tissues. Such target cells affected by the infection include, for example blood cells, and other target cells include hepatic cells, renal cells, brain cells, lung cells, epithelial cells and muscular cells. The tissues comprising these cells include lung, liver, kidney, arterial and venous veins, stomach, intestine, urethra, skin and muscle.

The vaccine of the present invention as the pharmaceutical composition in the above (3) can be prepared as the composition comprising the pharmaceutically effective amount of the recombinant baculovirus (AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39) and the pharmaceutically acceptable carrier.

The vaccine can be prepared into a pharmaceutical composition form utilizing the acceptable as the pharmaceutical as with the pharmaceutical composition in the above (3) in accordance with the standard methods. The carrier can include, for example, physiologically acceptable solutions such as sterile saline and sterile buffered saline.

The vaccine (hereinafter, the formulation is the same as in the pharmaceutical composition) can be prepared as a liposome formulation comprising the recombinant baculovirus (AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39) as the active ingredient, and can be combined with an adjuvant. Specific examples of the vaccine (pharmaceutical composition) of the present invention can include the liposome formulation. The liposome formulation can be one in which the recombinant baculovirus of the present invention has been retained in the liposome using acidic phospholipid as a membrane component or using neutral phospholipid and acidic phospholipid as the membrane component.

The neutral phospholipid and acidic phospholipid used as the membrane component are not particularly limited, and various lipids commonly used for the liposome formulation can be used alone or in mixture of two or more.

A liposome membrane is formed in accordance with the standard methods using the acidic phospholipid alone or combining the neutral phospholipid and the acidic phospholipid. In the case of combining the neutral phospholipid, the rate of the acidic phospholipid to be combined may be about 0.1 to 100 mol %, preferably 1 to 90 mol % and more preferably about 10 to 50 mol % in the liposome membrane components.

When the above liposome is prepared, for example cholesterol can be added. This can control the fluidity of the phospholipid and make the preparation of the liposome easier. The cholesterol is typically added at the amount equivalent to that of the phospholipid, and preferably it is preferable to add and combine at the amount 0.5 times to equivalent to that of the phospholipid.

For the rate of the active ingredient and the acidic phospholipid in the liposome formulation, the rate of the acidic phospholipid is about 0.5 to 100 equivalents, preferably about 1 to 60 equivalents and more preferably about 1.5 to 20 equivalents relative to the active ingredient.

The amount of the recombinant baculovirus of the present invention which is the active ingredient to be used can be several mol % to several tens mol %, preferably about 5 to 10 mol % and typically around 5 mol %.

The production, concentration and particle diameter control of the above liposome formulation can be performed in accordance with the standard methods. Various additives described above can also be combined with the liposome formulation if desired. Fatty acid (e.g., behenic acid, stearic acid, palmitic acid, myristic acid, oleic acid), alkyl group, cholesteryl group and the like can also be bound thereto and used. The production of the liposome formulation prepared by binding them can also be performed in accordance with the standard methods (see Long Circulating Liposomes: old drugs, New therapeutics., M. C. Woodle, G. Storm, Eds: Springer-Verlag Berlin (1998)).

The vaccine (pharmaceutical composition) of the present invention can be preferably used as a vaccine composition. When it is used, it is preferable for enhancing an anti-infection (anti-malaria or anti-influenza) effect to be combined with the adjuvant in pharmaceutically effective amount.

As the adjuvant, any ones commonly used for this type of vaccine can be used without limitation. As examples thereof, Freund's complete adjuvant, muramyl dipeptide, aluminium hydroxide, BCG, IL-12, N-acetylmuramine-L-alanyl-D-isoglutamine, thymosin α1 and QS-21 can be exemplified. The amount of the adjuvant to be combined can be appropriately determined depending on softening, erythema of skin, fever, headache and muscular pain which are likely expressed as a part of the immune response in the human beings or the animal after the administration thereof. The vaccine (pharmaceutical composition) of the present invention can be combined with other publicly known pharmaceutical articles such as immune response-facilitating peptide and antibacterial agents (synthetic antibacterial agents).

Optional drugs and additives can be further contained in the vaccine (pharmaceutical composition). As examples thereof, the drug such as calcium ion which aids intracellular uptake of the recombinant baculovirus of the present invention can be exemplified. The drugs and additives, e.g., the liposome, and for example, fluorocarbon emulsifier, cochleate, tubule, golden particles, biodegradable microsphere and cationic polymers which make the transfection easy can be used.

The amount of the active ingredient contained in the vaccine (pharmaceutical composition) (formulation) of the present invention is not particularly limited and can be selected from the wide range as long as it is the pharmaceutically effective amount. The dosage of the vaccine (pharmaceutical composition) is not particularly limited, and can be appropriately selected from the wide range depending on the desired therapeutic effect, the administration method (administration route), the therapeutic period, age and gender of the patient, and other conditions.

When the recombinant baculovirus which is the active ingredient of the vaccine (composition) of the present invention is administered to the human being, in terms of PFU of the recombinant virus, the recombinant baculovirus corresponding to $10^2$ to $10^{12}$ PFU, preferably $10^5$ to $10^{10}$ PFU and more preferably $10^6$ to $10^9$ PFU per patient is administered.

The dosage of the recombinant baculovirus (AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39) which is the active ingredient of the vaccine (pharmaceutical composition) of the present invention is selected from the very wide range as the amount of expressible DNA introduced into the vaccine host or the amount of transcribed RNA. Their amounts also depend on strength of transcription and translation promoters used for the transfer vector.

The vaccine (pharmaceutical composition) of the present invention is administered by directly injecting a recombinant baculovirus suspension in which the vector has been suspended in PBS (phosphate buffered saline) or saline into a local site (e.g., in lung tissue, in liver, in muscle and in brain), inhaling through nose or airway, or administering in blood vessel (e.g., intra-arterial, intravenous, and in portal vein). The vaccine of the invention is preferably administered by inhalation.

It is preferable that the vaccine (pharmaceutical composition) of the present invention is administered not once but once to multiple times by observing the state after the initial administration and administering the additional vaccine(s). This makes it possible to enhance the desired effect. It is possible to additionally immunize with the pharmaceutical composition composed of the recombinant baculovirus (AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39) of the present invention after administering the vaccine (pharmaceutical composition). The combination of the above various drugs to be combined also has the possibility to enhance the therapeutic effect by the administration of the vaccine (pharmaceutical composition).

In one embodiment of the vaccine (pharmaceutical composition) of the present invention, the recombinant baculovirus which is one of the active ingredient of the vaccine (pharmaceutical composition) of the present invention can be formulated by mixing the recombinant baculovirus obtained by homologous recombination of the transfer vector in which the fusion gene obtained by fusing the desired immunogenic foreign gene and the gene encoding the protein capable of being the component of the viral particle has been introduced with the baculovirus DNA in the form capable of injecting a unit dose (solution, suspension or emulsion) with the pharmaceutically acceptable carrier (i.e., non-toxic for the vertebrates including the human beings in the dosage and concentration to be administered, and compatible with other ingredients in the formulation). For example, the formulation preferably contains no antioxidant and no other compounds publicly known to be harmful for the recombinant baculovirus.

The carrier appropriately contains the additives in small amounts, such as substances which augment an isotonic property and a chemical stability. Such substances are non-toxic for the mammals including the human beings in the dosage and concentration to be administered, and can include buffers such as phosphoric acid, citric acid, succinic acid, acetic acid and other organic acids or salts thereof, antioxidants such as ascorbic acid, low molecular weight (e.g., less than about 10 residues) polypeptides (e.g., polyarginine or tripeptide) proteins (e.g., serum albumin, gelatin, or immunoglobulin), amino acids (e.g., glycine, glutamic acid, aspartic acid or arginine), monosaccharides, disaccharides and other carbohydrates (including cellulose or derivatives thereof, glucose, mannose, or dextrin), chelating agents (e.g., EDTA), sugar alcohols (e.g., mannitol or sorbitol), counterions (e.g., sodium), and/or nonionic surfactants (e.g., polysorbate, poloxamer).

The pharmaceutical vaccine (composition) comprising the recombinant baculovirus can be stored representatively in a unit or multiple dose container, e.g., a sealed ampoule or a vial as an aqueous solution or a lyophilized product.

The pharmaceutical composition comprising the vaccine (composition) of the present invention is administered in a mode identical to Good Medical Practice with considering a clinical condition (e.g., condition to be prevented or treated) of an individual patient, a delivered site of the vaccine (composition) comprising the recombinant baculovirus, a targeted tissue, the administration method, a regimen and other factors publicly known to those skilled in the art. Therefore, the proper dosage of the vaccine (composition) herein is determined in consideration of the above.

EXAMPLES

The present invention will be described below in more detail with reference to Examples. These Examples are exemplifications only and do not limit the present invention.

Example 1

Transfer Vector Plasmid and Method for Production Thereof of the Present Invention (1) Construction of Transfer Vector Plasmid pTriEx-Hsp65-gp64 of the Present Invention
(1.1) Construction of Plasmid pBACsurf-CSP A plasmid pcDNA-CS87 was made by obtaining a NheI-NotI fragment comprising the sequence fusing genomic DNA from *Plasmodium berghei* ANKA strain, a signal sequence of murine Igk secretion and a FLAG sequence in accordance with Yoshida et al's method (Yoshida, S., et al., B.B.R.C., 271, 107-115 (2000) and inserting the NheI-NotI fragment in a NheI-NotI site of pcDNA3.1 (supplied from Invitrogen).

A blood sample was collected from a BALE/c mouse infected with malaria parasite *P. berghei* ANKA, and *P. berghei* genomic DNA was extracted using QIAamp DNA Midi Kit (supplied from Qiagen). Subsequently, the *P. berghei* ANKA genomic DNA was amplified by PCR using a primer pbCSP1: 5'-GGAGG GCTAGCATGGAGACAGACACA CTCCTGCTATGGG-TACTGCTGCTCTG GGTTCCAGGTTCCACTGGT-GACGCGGATCCACTGCAG GACTACAAGGACGTAGACAAGGGATATG GACAAAATAAAGCATCCAAGCCC-3' (SEQ ID NO:1) (a NheI site newly made is represented by an underline, the signal sequence of murine Igk secretion is represented by Italic and the FLAG sequence is represented by a double underline) and PbCSP-R1: GGAGG GCGGCCGCATCCCGGGTTTT CTTATTTGAAC-CTTTTCGTTTTCTAACTCTTATACCAGAA CC-3' (SEQ ID NO:2) (a NotI site newly made is represented by the underline). The PCR was performed using PfuDNA polymerase (supplied from Stratagene) by 30 cycles (denaturing at 94° C. for 30 seconds, annealing at 55° C. for one minute and extending at 72° C. for 2 minutes). The PCR product does not have glycosyl phosphatidyl inositol (GPI) anchor and encodes PbCSP fused to the signal sequence of murine Igk secretion in place of its original signal sequence.

The PCR product was purified, cleaved with restriction enzymes NheI/NotI, which was then inserted in the NheI/NotI sites of pcDNA3.1 (supplied from Invitrogen), and a resulting plasmid was designed as pcDNA-CS87. The pcDNA-CS87 plasmid contains a CMV promoter, the signal sequence of murine Igk secretion, a protein (corresponding to 21 to 299 amino acids) encoded by the PbCSP gene, a poly A signal derived from a bovine growth hormone gene and a poly A sequence.

A gene fragment encoding an amino acid sequence at positions 21 to 306 of a peptide from PbCSP was obtained by cleaving the pcDNA-CS87 with the restriction enzymes PstI and SmaI, the DNA fragment was inserted in the PstI and SmaI sites of pBACsurf (supplied from Novagen), and the constructed plasmid was designed as pBACsurf-CSP.
(1.2) Construction of Plasmid pBACsurf-Hsp65

An Hsp65 gene was obtained by extracting genomic DNA from *M. tuberculosis* H37Rv strain using QIAamp DNA Midi Kit (supplied from Qiagen) and cloning by PCR. That is, the genomic DNA extracted from *M. tuberculosis* H37Rv strain was amplified by PCR using a primer, phsp65-F1: 5'-AATAAT<u>AGATCT</u>AATGGCCAAGACAATTGCGTA CGACGAAGA-3 (SEQ ID NO:3) (a BglII site is represented by the underline) and phsp65-R1: AATCCAAT <u>GCGGCCGC</u>GGGAATTCGATT CCTGCAGGTCA-GAAATCCATGCCACCCATGTCGCC-3 (SEQ ID NO:4) (the NotI site is represented by the underline).

The PCR product was purified, cleaved with the restriction enzymes BglII/NotI, ligated to the BamHI/NotI sites in pcDNA3.1 (supplied from Invitrogen), and the resulting plasmid was designated as pcDNA-hsp65.

The pcDNA-hsp65 plasmid is a construct in which the signal sequence of murine Igk secretion was fused to the hsp65 gene.

The PCR was performed with pcDNA-hsp65 as a template using the primer phsp65-F2: 5-CACC CCTGCAGGACTACAAGGACGACGATGACAAG GAATTCATGGCCAAGAC AATTGCGTACGACGAA-GAGGCC-3' (SEQ ID NO:5) (Sse8387I, EcoRI sites are represented by underlines, and the FLAG sequence is represented by Italic), and phsp65-R2: (5'-<u>CCCGGGC</u> GAAATC-CATGCCACCCATGTCGCCGCCACC-3' (SEQ ID NO:6) (a Cfr9I site is represented by the underline). The resulting Hsp65 gene DNA fragment (about 1660 bp) was cloned into pENTR/D-TOPO (supplied from Invitrogen), subsequently cleaved with Sse8387I/Cfr9I, which was then inserted in the PstI/Cfr9I sites of pBACsurf-CSP (Yoshida et al. Virology 316: 161-70, 2003) obtained above.

The plasmid constructed as the above was designed as pBACsurf-Hsp65.
(1.3) Construction of Plasmid pENTR-gp64

The PCR was performed with pBACgus-1 (supplied from Novagen) as the template using the primer pPolh-F2: 5'-CACC<u>CGGACCGG</u>ATAATTAAAAT ATAAC-CATCTCGCAAATAAATAAG-3' (SEQ ID NO:7) (a RsrII site is represented by the underline), and pgp64-R2: 5'-<u>GGTACC</u>ATATTGTCTATTACGGTTTCTAATCATAC-3' (SEQ ID NO:8) (a KpnI site is represented by the underline). The resulting gp64 gene DNA fragment (about 1700 bp) was inserted in pENTR/D-TOPO to construct the plasmid pENTR-gp64.

The plasmid constructed as the above was designated as pENTR-gp64.
(1.4) Construction of Transfer Vector pDual-Hsp65-gp64 of the Present Invention pDual-Hsp65-gp64 was cleaved with PstI/Cfr9I, and the hsp65 gene DNA fragment (about 1660 bp) was inserted in the PstI/Cfr9I sites of pENTR-gp64 to construct the plasmid pENTR-Hsp65-gp64.

Furthermore, pENTR-hsp65-gp64 was cleaved with RsrII/KpnI, and a DNA fragment (about 3360 bp) composed of a polyhedrin promoter and the hsp65gp64 gene was inserted in RsrII/KpnI of TriEx-3 (supplied from Novagen) to construct the transfer vector plasmid pDual-Hsp65-gp64 in which the expression was controlled by the desired dual promoters.

(2) Construction of Transfer Vector pDual-PbCSP-gp64 of the Present Invention

The plasmid pBACsurf-CSP obtained in (1.1.1) was cleaved with PstI/Cfr9I, and a PbCSP gene DNA fragment (about 890 bp) was inserted in the PstI/Cfr9I sites of pDual-Hsp65-gp64 to construct the plasmid pDual-PbCSP-gp64.

(3) Construction of Transfer Vector pDual-H1N1/HA1-gp64 of the Present Invention RNA was extracted from a culture supernatant of MDCK cells infected with influenza virus PR8/34 strain using QIAamp MiniElute Virus Spin Kit (QIAGEN), and amplified by RT-PCR using the primer HA-f: 5'-CCTGCAGGTATGAAGGCAAACCTACTGGTC-3' (SEQ ID NO:9) (a SbfI site is represented by the underline) and HA-r: 5'-GCCCGGGCGATGCATATTCTGCA-3 (SEQ ID NO:10) (a SbfI site is represented by the underline). The resulting influenza virus HA gene fragment with full length of 1700 by was cloned into pCR-Blunt II-TOPO (supplied from Invitrogen).

The resulting plasmid was designed as pCR-Blunt-HA. The PCR was performed with the pCR-Blunt-HA as the template using the primer pHA-F1: 5'-CACCGAATTC GACA-CAATATGTATAGGCTACCATGCG-3'(SEQ ID NO:11) (an EcoRI site is represented by the underline) and pHA-R1: 5'-CCCGGGCACCTCTGGATTGGATGGACGGAATG-3' (SEQ ID NO:12) (a Cfr9I site is represented by the underline). The resulting H1N1/HA1 gene DNA fragment (about 1000 bp) was cloned into pENTR/D-TOPO (supplied from Invitrogen), subsequently cleaved with EcoRI/Cfr9I, which was then inserted in the EcoRI/Cfr9I sites of pDual-Hsp65-gp64 to construct the plasmid pDual-H1N1/HA1-gp64.

(4) Construct of Transfer Vector pDual-PbTRAMP-gp64 of the Present Invention

The blood sample was collected from a BALB/c mouse infected with malaria parasite *P. berghei* ANKA, and *P. berghei* genomic DNA was extracted using QIAamp DNA Midi Kit (supplied from Qiagen).

A PbTRAMP gene was cloned by PCR with this genomic DNA as the template according to the following method. That is, the PCR was performed using the primer pTRAMP-F1: 5'-CACC GAATTCAAAATTGATACGAAAAAAAATGAAG-3' (SEQ ID NO:13) (the EcoRI site is represented by the underline) and pTRAMP-R1: CCCGGGCTTTTAATTTTGAGGAGTCTTTATTTTC-3' (SEQ ID NO:14) (the Cfr9I site is represented by the underline). The resulting PbTRAMP DNA fragment (about 800 bp) was cloned into pENTR/D-TOPO (supplied from Invitrogen), subsequently cleaved with EcoRI/Cfr9I, which was then inserted in the EcoRI/Cfr9I sites of pBACsurf-Hsp65. The constructed plasmid was designated as pBACsurf-Pb-TRAMP.

Subsequently, the pBACsurf-PbTRAMP was cleaved with EcoRI/Cfr9I, and a PbTRAMP gene DNA fragment (about 860 bp) was inserted in the EcoRI/Cfr9I sites of pDual-Hsp65-gp64 to construct the plasmid pDual-PbTRAMP-gp64.

(5) Construction of Transfer Vector pDual-PbAMA1D123-gp64 of the Present Invention The blood sample was collected from the BALE/c mouse infected with malaria parasite *P. berghei* ANKA, and the *P. berghei* genomic DNA was extracted using QIAamp DNA Midi Kit (supplied from Qiagen).

A PbAMA1 gene domain 123 (D123) gene was cloned by PCR with this genomic DNA as the template according to the following method. That is, the PCR was performed using the primer pAMA-F1: 5'-CACC GAATTCAATCCATGGGAAAA GTATACG-GAAAAATAT-3' (SEQ ID NO:15) (the EcoRI site is represented by the underline) and pAMA-R1: 5'-CCCGGG CTTCTCTGGTTTGATGGGCTTTCATATGCAC-3' (SEQ ID NO:16) (the Cfr9I site is represented by the underline). The resulting PbAMA1D123 DNA fragment (about 1280 bp) was cloned into pENTR/D-TOPO (supplied from Invitrogen), subsequently cleaved with EcoRI/Cfr9I, which was then inserted in the EcoRI/Cfr9I sites of pBACsurf-Hsp65. The constructed plasmid was designated as pBACsurf-PbAMA1D123.

Subsequently, the pBACsurf-PbAMA1D123 was cleaved with EcoRI/Cfr9I, and the PbAMA1D123 gene DNA fragment (about 1280 bp) was inserted in the EcoRI/Cfr9I sites of pDual-Hsp65-gp64 obtained in the above (1.4) to construct the plasmid pDual-PbAMA1D123-gp64.

(6) Construction of Transfer Vector pDual-PbMSP119-gp64 of the Present Invention The blood sample was collected from the BALB/c mouse infected with malaria parasite *P. berghei* ANKA, and the *P. berghei* genomic DNA was extracted using QIAamp DNA Midi Kit (supplied from Qiagen).

A PbMSP119 gene was cloned by PCR with this genomic DNA as the template according to the following method. That is, the PCR was performed using the primer pMsp1-F1: 5'-CACCCTGCAGGACTACAAGGACGACGATGA CAAGCACATAGCCTCAATAGCTTTAAATAACTTAA ATAAATCTGG-3' (SEQ ID NO:17) (the PstI site is represented by the underline) and pMsp1-R1: 5'-CCCGGG TTC-CCATAAAGCTGGAAGAGCTACAGAATACACC-3' (SEQ ID NO:18) (the Cfr9I site is represented by the underline). The resulting PbMSP119 DNA fragment (about 450 bp) was cloned into pENTR/D-TOPO (supplied from Invitrogen), subsequently was cleaved with PstI/Cfr9I, which was then inserted in the PstI/Cfr9I sites of pBACsurf-Hsp65. The constructed plasmid was designated as pBACsurf-PbMSP119.

Subsequently, the pBACsurf-PbMSP119 was cleaved with PstI/Cfr9I, and the PbMSP-119 gene DNA fragment (about 450 bp) was inserted in the PstI/Cfr9I sites of pDual-Hsp65-gp64 to construct the plasmid pDual-PbMSP-119-gp64.

(7) Construction of Transfer Vector pDual-PfCSP-gp64 of the Present Invention

The genomic DNA of falciparum malaria parasite, *P. falciparum* was extracted from human erythrocytes infected with *P. falciparum* 3D7 strain using QIAamp DNA Midi Kit (QIAGEN). A PfCSP gene was cloned by PCR with this genomic DNA as the template according to the following method. That is, the PCR was performed using the primer pPfCSP-F1: 5'-CACC GAATTCTTATTCCAGGAATACCAGTG CTATGGAAGT-3' (SEQ ID NO:19) (the EcoRI site is represented by the underline) and pPfCSP-R1: 5'-CCCGGGCTTTTTCCATTTTACAAATTTTTTTTTC-3' (SEQ ID NO:20) (the Cfr9I site is represented by the underline). The resulting PfCSP DNA fragment (about 1100 bp) was cloned into pENTR/D-TOPO (supplied from Invitrogen), subsequently cleaved with EcoRI/Cfr9I, which was then inserted in the EcoRI/Cfr9I sites of pDual-PbAMA1D123-gp64. The constructed plasmid was designated as pDual-PfCSP-gp64.

(8) Construction of Transfer Vector pDual-PfAMA1-gp64 of the Present Invention

The genomic DNA of falciparum malaria parasite, *P. falciparum* was extracted from human erythrocytes infected with *P. falciparum* 3D7 strain using QIAamp DNA Midi Kit (QIAGEN). The PfAMA1 gene was cloned by PCR with this genomic DNA as the template according to the following method. That is, the PCR was performed using the primer pPfAMA1-F1: 5'-CACC CTGCAGGACTACAAGGACGACGA TGACAAGCA- GAATTATTGGGAACATCCATAT CAAAATAGTGAT- GTG-3' (SEQ ID NO:21) (the PstI site is represented by the underline, the FLAG sequence represented by Italic) and pPfAMA1-R1: 5'-CCCGGG CTTTCATTTTATCATAAGT- TGGTTTATG-3' (SEQ ID NO:22) (the Cfr9I site is represented by the underline). The resulting PfAMA1 DNA fragment (about 3500 bp) was cloned into pENTR/D-TOPO (supplied from Invitrogen), subsequently cleaved with PstI/Cfr9I, which was then inserted in the PstI/Cfr9I sites of PbAMA1D123-gp64. The constructed plasmid was designated as pDual-PfAMA1-gp64.

(9) Construction of Transfer Vector pDual-Pfs25-gp64 of the Present Invention

The genomic DNA of falciparum malaria parasite, *P. falciparum* was extracted from human erythrocytes infected with *P. falciparum* 3D7 strain using QIAamp DNA Midi Kit (QIAGEN). The Pfs25 gene was cloned by PCR with this genomic DNA as the template according to the following method. That is, the PCR was performed using the primer pPfs25-F1: 5'-CACCGAATTCAAAGTTACCGTGGAT ACTGTATGCAAAAGAGGA-3' (SEQ ID NO:23) (the EcoRI site is represented by the underline), and pPfs25-R1: 5'-CCCGGGCAGTACATATAGAGCTTTCATTATCTAT-3' (SEQ ID NO:24) (the Cfr9I site is represented by the underline). The resulting Pfs25 DNA fragment (about 530 bp) was cloned into pENTR/D-TOPO (supplied from Invitrogen), subsequently cleaved with EcoRI/Cfr9I, which was then inserted in the EcoRI/Cfr9I sites of PbAMA1D123-gp64. The constructed plasmid was designated as pDual-Pfs25-gp64.

(10) Construction of Transfer Vector pDual-H5N1/HA1-gp64 of the Present Invention An HA1 gene is synthesized from bird influenza virus H5N1, and inserted in the EcoRI/Cfr9I sites of pDual-Hsp65-gp64 to construct the plasmid pDual-H5N1/HA1-gp64.

(11) Construction of Transfer Vector pDual-SARS/S-gp64 of the Present Invention

An S gene of SARS virus is synthesized and inserted in the EcoRI/Cfr9I sites of pDual-Hsp65-gp64 to construct the plasmid pDual-SARS/S-gp64.

(12) Construction of Transfer Vector pCP-H1N1/HA1-gp64 of the Present Invention

The PCR was performed with pCR-Blunt-HA as the template using Polh-f RsrII (5'-GGG CGGACCGGATAATTAAAATGATAACCATCTCG-3': SEQ ID NO:25) (the RsrII site is represented by the underline) and GP64-r DraIII (5'-GGG CACTTAGTGATATTGTCTATTACGGTTTCTAATC-3': SEQ ID NO:26) (the DraIII site is represented by the underline). A resulting DNA fragment of 2700 by was linked to a vector obtained by digesting pDual-H1N1/HA1-gp64 with the restriction enzymes RsrII and DraIII to construct pCP-H1N1/HA1-gp64.

(13) Construction of Transfer Vector pCAP-H1N1/HA1-gp64 of the Present Invention HA1 obtained by cleaving pCP-H1N1/HA1-gp64 with the restriction enzymes RsrII and DraIII and a gp64 gene fragment were inserted in the vector obtained by cleaving pTriEx-1.1 (supplied from Novagen) with the restriction enzymes RsrII and DraIII to construct a plasmid pCAP-H1N1/HA1-gp64.

(14) Construction of Transfer Vector pCU-H1N1/HA1-gp64 of the Present Invention

The PCR was performed with pTriEx3.1 as the template using CMVenh-f FseI (5'-GGG GGCCGGCCCTAGTTATTAATAGTAATCAATTAC-3': SEQ ID NO:27) (the FseI site is represented by the underline) and CMVenh-r KpnI (5'-GGG GGTACCCATGGTAATAGCGATG ACTAATACG-3': SEQ ID NO:28) (the KpnI site is represented by the underline) to amplify a CMV enhancer region. In addition, the PCR was performed with human genomic DNA as the template using UBBp-f KpnI (5'-GGG GGTACCTCGAGGAAGGTTTCTTCAACTC-3': SEQ ID NO:29) (the KpnI site is represented by the underline) and UBBp-r RsrII (5'-GGG CGGTCCGGACCTAGTTTAAAAGTAAAACATAAG-3': SEQ ID NO:30) (the RsrII site is represented by the underline) to amplify an UBB promoter region. Resulting two fragments were linked to the vector obtained by digesting pCP-H1N1/HA1-gp64 with the restriction enzymes FseI and RsrII to construct pCU-H1N1/HA1-gp64.

(15) Construction of Transfer Vector pDual-H1N1/NP-gp64 of the Present Invention The RT-PCR was performed with genomic RNA from influenza virus PR8/34 strain as the template using NP-f EcoRI (5'-ACGGAATTCCATTCAATTCAAACTGGA-3': SEQ ID NO:31 (the EcoRI site is represented by the underline) and NP-r Cfr9I (5'-GAT CCCGGGCCTTGTCAATGCTGAATGGCAA-3': SEQ ID NO:32) (the Cfr9I site is represented by the underline). A resulting fragment was digested with the restriction enzymes EcoRI and Cfr9I, and inserted in pCP-H1N1/HA1-gp64 digested with the restriction enzymes EcoRI and Cfr9I to make pDual-H1N1/NAe-gp64.

(16) Construction of Transfer Vector pDual-H1N1/M2-gp64 of the Present Invention The RT-PCR was performed with genomic RNA from influenza virus PR8/34 strain as the template using M2-f EcoRI (5'-CGGAATTCATGAGTCTTCTAACCGAGG-3': SEQ ID NO:33) (the EcoRI site is represented by the underline) and M2-r Cfr9I (5'-GAT CCCGGGCCTCCAGCTCTATGCTGAC-3': SEQ ID NO:34) (the Cfr9I site is represented by the underline). A resulting fragment was digested with the restriction enzymes EcoRI and Cfr9I, and inserted in pCP-H1N1/HA1-gp64 digested with the restriction enzymes EcoRI and Cfr9I to make pDual-H1N1/M2-gp64.

(17) Construction of Transfer Vector pDual-H1N1/NAe-gp64 of the Present Invention The RT-PCR was performed with genomic RNA from influenza virus PR8/34 strain as the template using NAe-f EcoRI (5'-ACGGAATTCCATTCAATTCAAACTGGA-3': SEQ ID NO:35) (the EcoRI site is represented by the underline) and NAe-r Cfr9I (5'-GAT CCCGGGCCTTGTCAATGCTGAATGGCAA-3': SEQ ID NO:36) (the Cfr9I site is represented by the underline). A resulting fragment was digested with the restriction enzymes EcoRI and Cfr9I, and inserted in pCP-H1N1/HA1-gp64 digested with the restriction enzymes EcoRI and Cfr9I to make pDual-H1N1/NAe-gp64.

(18) Construction of Transfer Vector pDual-M2e-gp64 of the Present Invention

The PCR was performed with pDual-H1N1/M2-gp64 as the template using M2-f EcoRI (5'-CG GAATTCATGAGTCTTCTAACCGAGG-3': SEQ ID NO:37) (the EcoRI site is represented by the underline) and M2e-r Cfr9I (5'-GAT CCCGGGCATCACTTGAACCGTTGCA-3': SEQ ID NO: 38) (the Cfr9I site is represented by the underline). A resulting fragment was digested with the restriction enzymes EcoRI and Cfr9I, and inserted in pCP-H1N1/HA1-gp64 digested with the restriction enzymes EcoRI and Cfr9I to make pDual-M2e-gp64.

(19) Construction of Transfer Vector pCP-HA1/NC99-gp64 of the Present Invention

RNA was extracted from a frozen stock of influenza virus NewCaledonia99/20 (NC99) using QIAamp MiniElute Virus Spin Kit (QIAGEN), and the RT-PCR was performed using primers HA1-f EcoRI (5'-GAT GAATTCGACACAATATGTATAGGCTACC-3': SEQ ID NO:39) (the EcoRI site is represented by the underline) and HA1-r CFr9I (NC99) (5'-GAT CCCGGGCTCTGGATTGAATGGATGGGATG-3': SEQ ID NO:40) (the Cfr9I site is represented by the underline) to amplify an HA1 gene fragment. A resulting fragment and pCP-H1N1/HA1-gp64 were treated with the restriction enzymes EcoRI and Cfr9I to newly insert the HA1 gene fragment derived from NC99 in an HA1 introduction region of pCP-H1N1/HA1-gp64. A resulting plasmid was designated as pCP-HA1/NC99-gp64.

(20) Construction of Transfer Vector pCP-H1N1/HA0-gp64 of the Present Invention

The PCR was performed with pCR-Blunt-HA as the template using HA0-f EcoRI (5'-GGG GAATTCATGAAGGCAAACCTACTGG-3': SEQ ID NO:41) (the EcoRI site is represented by the underline) and HA2-r Cfr9I (5'-GATCCCGGGCGATGCATATTCTGCA-3': SEQ ID NO:42) (the Cfr9I site is represented by the underline) to amplify the full length HA gene. A resulting fragment and pCP-H1N1/HA1-gp64 were treated with the restriction enzymes EcoRI and Cfr9I to newly insert the HA0 gene fragment in the HA1 introduction region of pCP-H1N1/HA1-gp64. A resulting plasmid was designated as pCP-H1N1/HA0-gp64.

(21) Construction of Transfer Vector pCP-H1N1/HA2-gp64 of the Present Invention

The PCR was performed with pCR-Blunt-HA as the template using HA2-f EcoRI (5'-GAT GAATTCATATTTGGAGCCATTGCCG-3': SEQ ID NO:43) (the EcoRI site is represented by the underline) and HA2-r Cfr9I (5'-GATCCCGGGCGATGCATATTCTGCA-3': SEQ ID NO:44) (the Cfr9I site is represented by the underline) to amplify the full length HA gene. A resulting fragment and pCP-H1N1/HA1-gp64 were treated with the restriction enzymes EcoRI and Cfr9I to newly insert the HA2 gene fragment in the HA1 introduction region of pCP-H1N1/HA1-gp64. A resulting plasmid was designated as pCP-H1N1/HA2-gp64.

(22) Construction of Transfer Vector pCP-H1N1/HA1-vp39 of the Present Invention

The PCR was performed with baculovirus DNA attached to BacVector-2000 Transfection Kit (Novagen) as the template using vp39-f (5'-CTT ACTAGTATGGACTACAAGGACGACGATGACAAG GAATTCGG CGGCGGCGGCTCGGCGCTAGTGC-CCGTGGGT-3': SEQ ID NO:45) (the SpeI site is represented by the underline and the EcoRI site is represented by the double underline) and vp39-r (5'-CTT CACTTAGTGATGGTGATGATGGTGGTGCCCGGGG CTTTAAAGCTTGACGGCTATTCCTCCACC-3': SEQ ID NO:46) (the DraIII site is represented by the underline and the SmaI is represented by the double underline) to amplify a vp39 gene region. An amplified fragment and pDual-H1N1/HA1-gp64 were cleaved with the restriction enzymes SpeI and DraIII, and ligated one another to construct pDual-vp39. Furthermore, the PCR was performed with pDual-H1N1/HA1-gp64 as the template using Polh-S1 (5' GCTAACCAT-GTTCATGCC-3': SEQ ID NO:47) and HA1-r EcoRI (5'-GGGGAATTCACCTCTGGATTGGAT GGAC-3': SEQ ID NO:48) (the EcoRI site is represented by the underline). A resulting fragment was digested with EcoRI to prepare the HA1 gene. A resulting fragment was inserted in pDual-vp39 digested with EcoRI to construct pCP-H1N1/HA1-vp39.

(23) Construction of Transfer Vector pCP-H1N1/NP-vp39 of the Present Invention

The PCR was performed with pDual-H1N1/NP-gp64 as the template using NP-f 5EcoRI (5'-ACG GAATTCATGGCGTCCCAAGGCACC-3': SEQ ID NO:49) (the EcoRI site is represented by the underline) and NP-r EcoRI (5'-ACG GAATTCATTGTCGTACTCCTCTGCATTG-3': SEQ ID NO:50) (the EcoRI site is represented by the underline). A resulting fragment was digested with EcoRI. A resulting fragment was inserted in pDual-vp39 digested with EcoRI to construct pCP1-H1N1/NP-vp39.

Reference Example 1

Construction of pBACgus-CMV-PbCSP (1.1) Construction of pcDNA-GL3 (luc)
pGL3-Enhancer (Promega) was cleaved with the restriction enzymes HindIII/XbaI, a luciferase gene DNA fragment (about 1690 bp) was ligated to the HindIII/XbaI sites of pcDNA3.1 (supplied from Invitrogen), and the resulting plasmid was designated as pcDNA-GL3(luc).

(1.2) Construct of pBACgus-CMV-IgHsp65
pcDNA-hsp65 obtained in the above Example 1 (1.2) was cleaved with the restriction enzymes BamHI/NotI, and inserted in the BamHI/NotI sites to produce pcDNA-Ighsp65. The resulting plasmid was designated as pcDNA-IgHsp65.

Subsequently, the pcDNA-IgHsp65 was cleaved with BglII/SphI, and a gene cassette (about 2850 bp) composed of the CMV promoter, the Hsp65 gene carrying the murine Igk signal sequence, and the poly A signal derived from the bovine growth hormone was inserted in the BglII/SphI sites of pBACgus-1 (Novagen). The constructed plasmid was designated as pBACgus-CMV-Hsp65.

(1.3) Construction of pBACgus-CMV-GL3
The plasmid pcDNA-GL3(luc) obtained above was cleaved with the restriction enzymes NheI/XbaI, the luciferase gene DNA fragment (about 1690 bp) was inserted in the NheI/XbaI sites of the plasmid pBACgus-CMV-Hsp65, and the resulting plasmid was designated as pBACgus-CMV-GL3.

(1.4) Construction of pBACgus-CMV-PbCSP
A gene fragment encoding the amino acid sequence corresponding to positions 21 to 306 of the PbCSP peptide was yielded by cleaving the plasmid pBACsurf-CSP with the restriction enzymes PstI and SmaI, the DNA fragment (about 858 bp) was inserted in the PstI and SmaI sites of pBACgus-CMV-GL3 obtained above, and the resulting plasmid was designated as pBACgus-CMV-PbCSP.

(1.5) Construction of pBACgus-CMV-HA-Full
pCR-Blunt-HA was cleaved with BamHI/Sse83871, and an HA gene DNA fragment (about 1750 bp) was inserted in the BamHI/PstI site of pBluescript II (KS-) to construct the plasmid pBluescript-HA.

Furthermore, the pBluescript-HA was cleaved with HindIII/XbaI, and an HA gene DNA fragment (about 1800 bp) was inserted in the HindIII/XbaI sites of pBACgus-CMV-GL3 obtained in (1.3) to construct the plasmid pBACgus-CMV-HA-full.

Example 2

Recombinant Baculovirus and Method for Production Thereof of the Present Invention (1) The recombinant baculovirus was made using the kit (BacVector-2000 Transfection Kit supplied from Novagen)

for making the recombinant baculovirus, by co-transfecting BacVector-2000 DNA with each of the transfer vectors: pDual-Hsp65-gp64, pDual-PbCSP-gp64, pDual-H1N1/HA1-gp64, pDual-PbTRAMP-gp64, pDual-PbAMA1D123-gp64, pDual-PbMSP-119-gp64, pDual-PfCSP-gp64, pDual-PfAMA1-gp64, pDual-Pfs25-gp64, pCP-H1N1/HA1-gp64, pCAP-H1N1/HA1-gp64, pCU-H1N1/HA1-gp64, pDual-H1N1/NP-gp64, pDual-H1N1/M2-gp64, pDual-H1N1/NAe-gp64, pDual-M2e-gp64, pCP-HA1/NC99-gp64, pCP-H1N1/HA0-gp64, pCP-H1N1/HA2-gp64, pCP-H1N1/HA1-vp39, pCP-H1N1/NP-vp39 constructed in the above Example 1, and the plasmids, pBACgus-CMV-PbCSP and pBACgus-CMV-HA-full obtained in Reference Example 1 into Sf-9 cells.

The recombinant baculoviruses made were designated as AcNPV-Dual-Hsp65, AcNPV-Dual-PbCSP, AcNPV-Dual-H1N1/HA1, AcNPV-Dual-PbTRAMP, AcNPV-Dual-PbAMA1D123, AcNPV-Dual-PbMSP-119, AcNPV-CMV-PbCSP, AcNPV-CMV-HA-full, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39, respectively.

The Sf-9 cells were cultured so as to become $2 \times 10^7$ cells per 150 mm plate for culture (sumilon supplied from Akita Sumitomo Bakelite Co., Ltd.), and each baculovirus described above was infected at an infection multiplicity of about 5. After 5 to 6 days, the medium was centrifuged at 10,000×g at 4° C. for 25 minutes to collect a supernatant, which was further centrifuged using a Beckman ultracentrifuge (SW28 swing rotor) at 25,000 rpm at 4° C. for 90 minutes to yield viral particles.

(2) The recombinant baculovirus can be made using the kit (BacVector-2000 Transfection Kit supplied from Novagen) for making the recombinant baculovirus, by co-transfecting BacVector-2000 DNA with each of the transfer vectors: pDual-H5N1/HA1-gp64 and pDual-SARS/S-gp64 constructed in the above Example 1 into the Sf-9 cells. The recombinant baculoviruses to be made is designated as AcNPV-H5N1/HA1 and AcNPV-Dual-SARS/S, respectively.

The Sf-9 cells were cultured so as to become $2 \times 10^7$ cells per 150 mm plate for culture (sumilon supplied from Akita Sumitomo Bakelite Co., Ltd.), and each baculovirus described above was infected at an infection multiplicity of about 5. After 5 to 6 days, the medium can be centrifuged at 10,000×g at 4° C. for 25 minutes to collect the supernatant, which can be further centrifuged using the Beckman ultracentrifuge (SW28 swing rotor) at 25,000 rpm at 4° C. for 90 minutes to yield viral particles.

Example 3

Pharmacological Effect Test of Recombinant Baculovirus of the Present Invention (Pharmacological Effect Test as Malaria Vaccine)
(Malaria Infection Prevention Test)
3. Experimental Methods
3.1 Vaccine Inoculation A recombinant virus solution for vaccine was inoculated to BALB/c female mice three times at three week intervals. In the case of injection into thigh muscle, the amount was 0.2 mL/body, and the virus solution was prepared so that the virus amount was $5 \times 10^6$ pfu/body.

3.2 Infection of Mice with Malaria

The mice in each group were anaesthetized with a anesthesia solution for mice, 3 weeks after the third vaccine inoculation, and infected with malaria by making *Anopheles stephensi* SDA 500 strain infected with *Plasmodium berghei* ANKA 2.34 clone bite the mice.

3.3 Calculation of Mouse Survival Rate in Each Group

After the infection with malaria, death cases in each group were counted, and the survival rate of the mice in each group was calculated.

3.4 For the malaria infection prevention effect of the pharmaceutical composition of the present invention as the vaccine, the results of the pharmacological effect test are shown in Table 1. The survival rate in each group was shown in right columns in Table 1.

As shown in Table 1, all of the mice in which the erythrocytes infected with malaria in peripheral blood had been identified were died within 38 days after the infection. Among the recombinant virus in which the antigen (CSP) gene in the sporozoite phase had been inserted, in the group (group No. 4) in which the recombinant baculovirus (Example 1 (2)) containing the transfer vector: AcNPV-Dual-PbCSP) obtained in Example 2 had been inoculated intramuscularly, 100% of the infection prevention effect was observed.

In the wild type baculovirus (group No. 2), no difference from the control group (group No. 1) was observed. In the group (group No. 3) in which the recombinant baculovirus obtained in Example 2 using the mammal promoter (AcNPV-CMV-PbCSP, including the vector in Reference Example 1) had been included, the slightly higher survival rate was observed compared with the control group, suggesting the probability that the effect by the virus inoculation appeared although it was weak.

TABLE 1

Survival rates of mice in each group

| Group No. | Survival/cases | Survival rate (%) |
|---|---|---|
| 1 None | 5/20 | 25 |
| 2 AcNPV-WT | 6/20 | 30 |
| 3 AcNPV-CMV-PbCSP | 5/10 | 50 |
| 4 AcNPV-Dual-PbCSP | 10/10 | 100 |

Example 4

Pharmacological Effect Test of Recombinant Baculovirus of the Present Invention (Pharmacological Effect Test as Influenza Virus Vaccine)
(Influenza Virus Infection Prevention Test)
4. Experimental Methods
4.1 Vaccine A virus solution for vaccine was inoculated twice at 2 week intervals. The vaccine virus was injected at 10" PFU per mouse in thigh muscle using a syringe with 26G for insulin injection.

4.2 Preparation of Virus Solution for Challenge

On a current day of the infection with influenza virus, a stored virus solution of the influenza virus A/PR/8/34 strain was naturally thawed at room temperature. The thawed stored virus solution was diluted to 1000 $TCID_{50}$/0.05 mL for lower respiratory tract infection and 1000 $TCID_{50}$/0.005 mL for upper respiratory tract infection using Dulbecco's Phosphate Buffer Saline: (D-PBS) containing 10% sterile BSA: bovine serum albumin to make the virus solution for challenge.

4.3 Intranasal Inoculation of Virus Solution

Two weeks after the second vaccine inoculation, the mice were anesthetized by intramuscularly administering 0.05 mL of the anesthesia solution for mice. The influenza virus solution made in 4.2 was inoculated in the nose of the mice at 0.005 mL for the upper respiratory tract infection or 0.05 mL for the lower respiratory tract infection.

4.4. Sampling of Lung

Three days after the virus inoculation, 0.1 mL per mouse of the anesthesia solution for mice was intramuscularly administered to 4 mice in each group, and euthanized by bleeding from aorta abdominalis under the anesthesia. Subsequently, the mice were anatomized, and the lung was sterilely removed.

4.5 Records of Survival Rate of the Mice after the Inoculation of Influenza Virus Until 11 days after the inoculation of influenza virus, the survival rate of the mice was confirmed and recorded once a day.

4.6 Preparation of Lung Homogenate and Dilution Solution

A lung homogenate was made by adding 3 mL of 0.1% BSA, 10 mM HEPES, Minimum Essential Medium (MEM, GIBCO) containing antibiotics and homogenizing using a polytron homogenizer. The lung homogenate was dispensed in cryotubes and stored in an ultralow temperature freezer.

A series of dilution of 10 times or $10^{0.5}$ times was made using the MEM medium to which the above antibiotics and trypsin (SIGMA, T-4549, 2 mg/mL) had been added.

4.7 Preparation of Medium for Cell Growth

The medium for cell growth (MEM+10% FBS) was prepared by adding 50 mL of fetal bovine serum: FBS to 500 ml of MEM, and stored in a refrigerator until use.

4.8 Culture of MDCK (Madin-Darby Canine Kidney) Derived from Canine Kidney

The frozen and stored MDCK cells were rapidly thawed in warmed water, then suspended in 10 mL of the medium for cell growth, and the supernatant was removed by centrifugation (1000 rpm, 5 minutes, 4° C.). A cell pellet collected by centrifugation was suspended in the medium for cell growth. The cells were seeded in a culture flask, and cultured in an incubator with 5% $CO_2$ at 37° C. After the start of the culture, morphology and growth of the cells were observed under a microscope, just before the MDCK cells became confluent, the cells were washed with D-PBS(−), the treatment with trypsin was given to the cells to disperse, and the cells were suspended in the medium for cell growth. The cell suspension was seeded in the culture flask, and the fresh medium for cell growth was added to make cell passage.

4.9 Preparation of Medium for Viral Growth (Maintenance Medium)

The medium in which BSA at 0.1% had been added to 500 mL of MEM (10 mM HEPES buffer was added) was rendered the medium for virus growth (MEM+0.1% BSA), and was stored in the refrigerator after the preparation until use. The antibiotics was added in use.

4.10 Measurement of Viral Infectivity Titer (Cytopathic Effect, CPE Method)

Just before the MDCK cells in the culture flask became confluent, the treatment with trypsin was given to the cells to disperse the cells, the number of the cells was counted, and a suspension of MDCK cells at $6 \times 10^5$ cells/mL was prepared using the maintenance medium. This was dispensed by 0.05 mL in each well of a 96-well plate, and cultured overnight in the $CO_2$ incubator with 5% $CO_2$ at 37° C.

On the subsequent day, it was confirmed that the cells adhered, and each lung homogenate dilution made previously was dispensed by 0.05 mL in each well for 6 wells in the 96-well plate, which was then cultured in the $CO_2$ incubator with 5% $CO_2$ at 37° C. for 3 days.

On the 3rd day of the culture, it was confirmed that the cells in the well are denatured, then a 30% formalin-containing crystal violet solution was dispensed by 0.05 mL in each well in the 96-well plate to fix and stain the cells, and the infectivity titer of the virus in the lung was calculated by Reed-Munch method.

4.11 Effects of Each Vaccine Group on Infectivity Titer of Virus In Vivo in the Mouse The infectivity titers in the murine lung homogenates in the control group (inoculated with AcNPV) and the test groups (inoculated with the recombinant baculovirus [including the transfer vector: AcNPV-Dual-H1N1/HA1 obtained in Example 1(3)] and the recombinant baculovirus [containing the vector: AcNPV-CMV-H1N1/HA full obtained in Reference Example 1]) were compared. Each viral infectivity titer was converted into logarithm. The therapeutic effect among the groups was analyzed by Tukey test (Release 8.1, SAS Institute Japan Ltd) considering its multiplicity.

Figure 1:
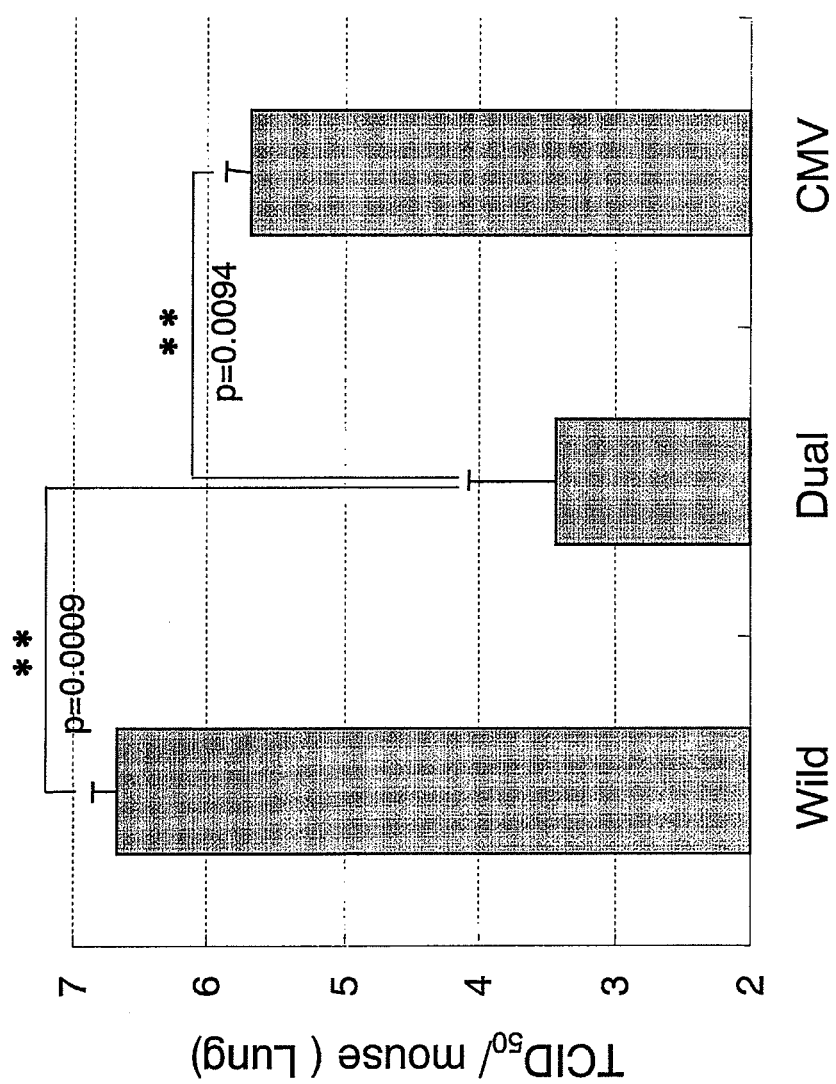
FIG. 1 is a view showing preventive effect (virus infectivity titer) of recombinant baculovirus AcNPV-Dual-H1N1/HA1 on infection with influenza virus.

The results are shown in FIG. 1.

Figure 2:
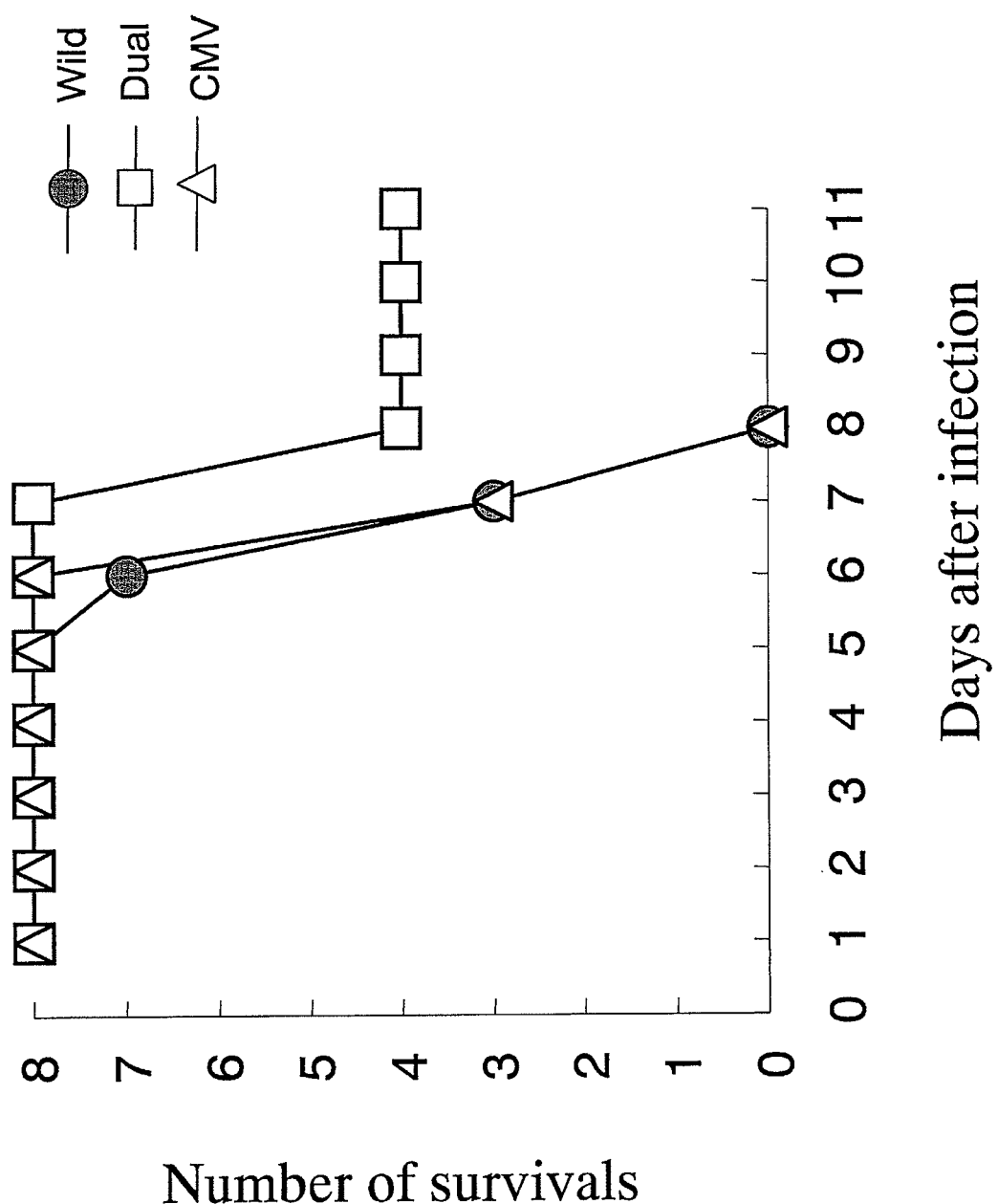
FIG. 2 is a view showing the preventive effect (survival period) of the recombinant baculovirus AcNPV-Dual-H1N1/HA1 on infection with influenza virus.

Effect of Each Vaccine on Survival Period after the Infection with Influenza Virus The survival periods in the control group (inoculated with AcNPV) and the vaccine groups (inoculated with AcNPV-Dual-H1N1/HA1 or AcNPV-CMV-H1N1/HA full) were compared using log rank test, and the results are shown in FIG. 2.

Statistical analysis was performed using SAS system (SAS Institute Japan, R. 8.1). A significant level was 5%.

4.12 Infectivity Titer of Virus in Lung

In the group in which AcNPV-Dual-H1N1/HA1 had been inoculated intramuscularly, the infectivity titer of the virus in lung on the day 6 after the infection was significantly inhibited ($p=0.0009$) compared with the control group (inoculated with AcNPV). Meanwhile, in the group in which AcNPV-Dual-H1N1/HA1 had been inoculated intramuscularly, the infectivity titer of the virus in lung on the day 6 after the infection was significantly inhibited ($p=0.0094$) compared with the group in which AcNPV-CMV-H1N1/HA full had been inoculated.

4.13 Survival Period

In the group in which AcNPV-Dual-H1N1/HA1 had been inoculated intramuscularly, the survival period was significantly prolonged ($p=0.0031$) compared with the control group (inoculated with AcNPV). Meanwhile, the survival period in the group in which AcNPV-CMV-H1N1/HA full had been inoculated was not significantly different ($p=0.7851$) from that in the control group (inoculated with AcNPV). The survival period in the group in which AcNPV-Dual-H1N1/HA1 had been inoculated intramuscularly was significantly prolonged ($p=0.0031$) compared with the group in which AcNPV-CMV-H1N1/HA full had been inoculated.

In this evaluation system, the mouse causes influenza virus pneumonia and dies. Thus, it can be speculated that growth of the virus in lung was inhibited to reduce the death of mouse from the pneumonia by inoculating AcNPV-Dual-H1N1/HA1 intramuscularly.

Example 5

Expression Test of Vaccine Antigen from Recombinant Baculovirus of the Present Invention in Insect Cells The Sf-9 cells were cultured at $3 \times 10^6$ cells per well in a 12-well plate, and baculovirus particles of AcNPV-Dual- PbCSP, AcNPV-Dual-HSP65 or AcNPV-Dual-H1N1/HA1 obtained in Example 2 or the wild type baculovirus, AcNPV-WT as the control were infected at infection multiplicity of about 5. After 3 to 4 days, the culture supernatant was removed, the plate was rinsed three times with PBS, and then 0.2 mL per well of Leamuli solution (Tris-hydrochloride pH 6.8, 2% SDS, 10% glycerol, 0.1% bromophenol blue) containing 2% 2-mercaptoethanol was added to completely lyse the cells. The sample was boiled at 95° C. for 5 minutes, and electrophoresed on SDS-PAGE. After the electrophoresis, the protein was transferred onto a PVDF membrane (Immobilon-P supplied from Millipore) and blocking was performed by immersing the membrane in block ace (supplied from Dai Nippon Pharmaceutical Co., Ltd.) at 4° C. for 12 hours. Western blotting was performed by the following procedure. The membrane to which the proteins from the Sf-9 cells infected with each baculovirus had been transferred was incubated with a mouse anti-FLAG monoclonal antibody (supplied from Sigma) as the primary antibody, and then incubated with a biotin-labeled goat anti-mouse IgG (H+L) antibody as the second antibody (supplied from Vector). Further, an avidin labeled alkaline phosphatase (supplied from GIBCO-BRL) was added and a color was developed with NBT/BCIP (supplied from GIBCO-BRL) to detect bands of the protein.

Figure 3:
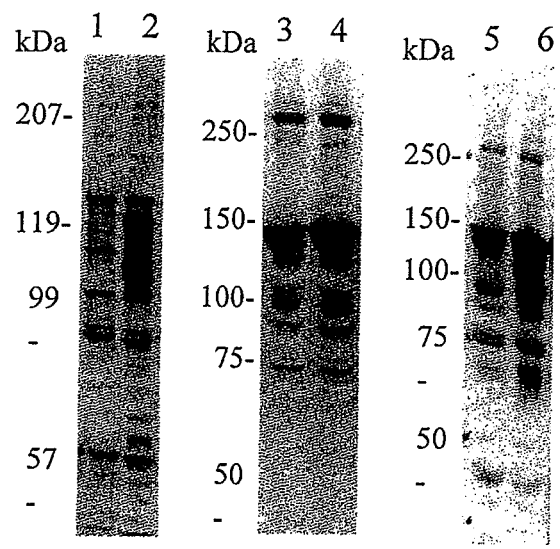
FIG. 3 is views showing Western blotting analysis of expression of a fusion product in infected insect cell by recombinant baculovirus the influenza virus HA gene (H1N1/HA1), the *M. tuberculosis* Hsp65 gene (Hsp65) or the malaria parasite CSP gene (PbCSP) produced from the transfer vector.

The results are shown in FIG. 3.

FIG. 3 shows Western blotting analysis showing the expression of the fusion antigen of the influenza virus HA gene, the *M. tuberculosis* Hsp65 gene and the malaria parasite CSP gene from the recombinant transfer vector in the recombinant baculovirus in the insect cells. In the figure, the lane 1 shows the bands from the wild type baculovirus (AcNPV-WT), the lane 2 shows bands from the recombinant baculovirus (AcNPV-Dual-H1N1/HA1) in which the influenza virus HA gene was inserted under the dual promoters of the present invention, the lane 3 shows the bands from the wild type baculovirus (AcNPV-WT), the lane 4 shows the bands from the recombinant baculovirus (AcNPV-Dual-Hsp65) in which the *M. tuberculosis* Hsp65 gene was inserted under the dual promoters of the present invention, the lane 5 shows the bands from the wild type baculovirus (AcNPV-WT), and the lane 6 shows the bands from the recombinant baculovirus (AcNPV-Dual-PbCSP) in which the malaria parasite CSP gene was inserted under the dual promoters of the present invention.

As shown in the lanes 2, 4 and 6 in the figure, the band corresponding to the expressed fusion product of the immunogenic foreign antigen gene and the gp64 gene is observed in the recombinant baculovirus in which each antigen gene and the gp64 gene were fused and expressed under the dual promoters of the present invention.

From this, it has been identified that the immunogenic foreign antigen gene and the gp64 gene can be fused and expressed in the insect cells.

Example 6

Expression Test of Vaccine Antigen from Recombinant Baculovirus of the Present Invention in Mammal HepG2 cells were infected with AcNPV-Dual-Hsp65, or AcNPV-WT as the control at an infection multiplicity of about 1. After 24 hours, the culture supernatant was removed, the plate was rinsed three times with PBS, and then an acetone ethanol solution (7:3) cooled at −20° C. was added to fix the cells at −20° C. for 5 minutes. The blocking was performed at room temperature by adding 5% normal goat serum (supplied from Sigma). Subsequently, a mouse anti-Hsp65 antibody (Yoshida et al., Vaccine 2005) as the primary antibody and then the FITC-labeled goat anti-mouse IgG (H+L) were added and incubated. The reacted cells were detected under a fluorescence microscope.

HepG2 cells were also cultured $1 \times 10^7$ cells per 100 mm plate for cell culture, and infected with the baculovirus particles, AcNPV-Dual-H1N1/HA1 or AcNPV-CMV-H1N1/HA full or AcNPV-WT as the control at an infection multiplicity of about 5. After 2 hours, the culture supernatant was removed, the plate was rinsed three times with PBS, and then the cells were cultured in the medium not containing methionine and cysteine (medium in which 10% FBS dialyzed against PBS was added to Dulbecco's Modified Eagle medium (Invitrogen)) for 3 hours. An isotope-labeled methionine and cysteine solution (TRANS35S-LABEL MP Biomedicals, Inc.) was added at a final concentration 5 µCi/mL. After 12 hours, the culture supernatant was removed, the plate was rinsed three times with PBS, and then the cells were lysed with 0.5 mL of RIPA buffer (1% Sodium deoxycholate, 1% Triton X-100, 0.1% SDS, 10 mM Tris-HCl [pH 7.5]) to make a sample. The sample was added to Protein A-Sepharose CL-4B (Pharmacia) carrier to which the serum from the mouse infected with influenza virus had been absorbed in advance, and incubated on ice for 2 hours. The carrier was washed 5 times with RIPA buffer, Leamuli solution containing 2% 2-mercaptoethanol was added, the sample was boiled at 95° C. for 5 minutes, and electrophoresed on 6% SDS-PAGE. After the electrophoresis, the gel was dried, and the protein reacted with the antibody was detected by autoradiography.

The results are shown in FIGS. 4 and 5.

FIG. 4 (A) shows the cells stained with the fluorescence labeled antibody showing the expression of the *M. tuberculosis* Hsp65 gene in the recombinant baculovirus in HepG2 cells.

FIG. 4 (B) shows the case in which the wild type baculovirus was added to HepG2 cells.

As is evident from (A) in the figure, it is found that the recombinant baculovirus using the transfer vector with the dual promoters of the present invention can express the objective antigen in the mammalian cells.

This suggests that when administered to the mammal including human beings, the recombinant baculovirus produced from the recombinant transfer vector of the present invention invades into the mammalian cells, the mammalian promoter is operated, and the objective foreign antigen gene and the gp64 gene are fused in the mammalian cells to induce the acquired immunity.

FIG. 5 shows immunoprecipitation analysis of the expression of the fusion antigen in the recombinant baculovirus in which the influenza virus HA antigen gene was incorporated under the dual promoters in the mammalian cells. In the figure, the lane 1 shows the wild type baculovirus (AcNPV-WT), the lane 2 shows the recombinant baculovirus (AcNPV-CMV-H1N1/HA full) in which the influenza virus HA antigen gene was incorporated under the CMV promoter, and the lane 3 shows the recombinant baculovirus (AcNPV-Dual-H1N1/HA1) in which the influenza virus HA antigen gene was incorporated to fuse with the gp64 gene and express under the dual promoter.

In the recombinant baculovirus (AcNPV-CMV-H1N1/HA full) in which the influenza virus HA antigen gene was incorporated under the CMV promoter and the recombinant baculovirus (AcNPV-Dual-H1N1/HA1) in which the influenza virus HA antigen gene was incorporated to fuse with the gp64 gene and express under the dual promoters, it is evident that the protein which specifically reacts with the serum infected with influenza virus, i.e., the protein including the HA antigen was newly synthesized in HepG2 cells.

From this, it is thought that the recombinant baculovirus of the present invention expresses the antigen protein encoded by the desired immunogenic foreign antigen gene even in the mammalian cells, and that when the recombinant virus is administered to the mammals including human beings, with the expression of the fusion antigen in human cells, the acquired Immunity specific for the antigen can be induced.

Example 7

Identification Test of Fusion Antigen in Vaccine Antigen Presented on Viral Particle (Virion) of Recombinant Baculovirus of the Present Invention To 0.005 mL of each virus concentration solution of the baculovirus particles, AcNPV-WT, AcNPV-CMV-PbCSP, AcNPV-PbCSPsurf or AcNPV-Dual-PbCSP collected by ultracentrifuge, 0.005 mL of Leamuli solution (2×) was added, which was then boiled at 95° C. for 5 minutes, and electrophoresed on 6% SDS-PAGE. After the electrophoresis, the proteins were transferred onto the PVDF membrane (Immobilon-P supplied from Millipore) and blocking was performed by immersing the membrane in block ace (supplied from Dai Nippon Pharmaceutical Co., Ltd.) at 4° C. for 12 hours. The Western blotting was performed by the following procedure. The membrane to which the viral particle proteins had been transferred was incubated with the mouse anti-FLAG monoclonal antibody (supplied from Sigma) as the primary antibody, and then incubated with the biotin-labeled goat anti-mouse IgG (H+L) antibody as the second antibody (supplied from Vector). Further, avidin-labeled alkaline phosphatase (supplied from GIBCO-BRL) was added and the color was developed with NBT/BCIP (supplied from GIBCO-BRL) to detect bands of the protein.

The results are shown in FIG. 6.

FIG. 6 shows the Western blotting analysis showing the expression of the malaria CSP gene (PbCSP) in the viral particles of the recombinant baculovirus made from the recombinant transfer vector. In the figure, the lane 1 shows the wild type baculovirus, the lane 2 shows the recombinant baculovirus made from the transfer vector in which the PbCSP antigen gene was inserted under the control of the mammalian promoter, the lane 3 shows the recombinant baculovirus made from the transfer vector in which the PbCSP antigen gene was inserted to fuse with the gp64 gene and express under the control of the baculovirus polyhedrin promoter, and the lane 4 shows the recombinant baculovirus made from the transfer vector in which the PbCSP antigen gene was inserted to fuse with the gp64 gene and express under the control of the dual promoters. The baculoviruses were electrophoresed and the expression product of the fused PbCSP gene and gp64 gene was identified.

As shown in the lanes 3 and 4, for AcNPV-PbCSPsurf and AcNPV-Dual-PbCSP, the strong band which indicated the presence of the fusion antigen was identified in the recombinant viral particles.

This way, from Example 7, it is found that in the recombinant baculovirus produced from the recombinant transfer vector of the present invention, the expression product of the fused gp64 gene to the desired immunogenic foreign gene can be present in the recombinant viral particles.

Example 8

Sustained Gene Expression by Exchange of Promoter

1) Sustained Gene Expression by Exchange of Promoter

In order to identify whether the recombinant virus sustains the antigen expression in cultured cells, HeLa cells were infected with AcNPV-CP-H1N1/HA1, AcNPV-CAP-H1N1/HA1 or AcNPV-CU-H1N1/HA1, and the antigen expression was identified. The cells were seeded in a 24-well plate at $1.0 \times 10^4$ cells/well, and then infected with the virus at MOI=10, 20, 100, which was adhered for one hour. Subsequently the virus was removed from a cell culture supernatant, and the cells were cultured in an incubator. The cells were collected with time, and RNA was extracted. RT-PCR was performed with the extracted RNA as the template using the primer HA1_F01 (5'-GAGCTGAGGGAGCAATTGAG-3' (sequence: SEQ ID NO: 51) and the primer HA1_R01 (5'-GGGTGATGAATACCCCACAG-3'(sequence: SEQ ID NO: 52). The amplified DNA was analyzed on electrophoresis.

As a result, the expression was identified in all three types, confirming that the CMV promoter can be converted to another eukaryotic promoter with respect to the recombinant baculovirus of the present invention.

FIG. 7 shows the results of detecting the gene expression in HeLa cells by RT-PCR. M represents DNA markers for electrophoresis. Samples are as follows:
1. RNA from cells infected with wild type virus at MOI=10;
2. RNA from cells infected with wild type virus at MOI=20;
3. RNA from cells infected with wild type virus at MOI=100;
4. RNA from cells infected with AcNPV-CP-H1N1/HA1 at MOI=10;
5. RNA from cells infected with AcNPV-CP-H1N1/HA1 at MOI=20;
6. RNA from cells infected with AcNPV-CP-H1N1/HA1 at MOI=100;
7. RNA from cells infected with AcNPV-CU-H1N1/HA1 at MOI=10;
8. RNA from cells infected with AcNPV-CU-H1N1/HA1 at MOI=20;
9. RNA from cells infected with AcNPV-CU-H1N1/HA1 at MOI=100;
10. RNA from cells infected with AcNPV-CAP-H1N1/HA1 at MOI=10;
11. RNA from cells infected with AcNPV-CAP-H1N1/HA1 at MOI=20; and
12. RNA from cells infected with AcNPV-CAP-H1N1/HA1 at MOI=100.

The sample was collected with time 0 hour, one day, 4 days and 7 days after the infection, was amplified by RT-PCR, and amplified DNA was electrophoresed.

Example 9

Antibody Titer and Cellular Immunity Induced by PbCSP Antigen Recombinant Virus

1. Vaccine Inoculation

A solution of the recombinant virus for vaccination was inoculated to BALB/c female mice three times at three week intervals. An inoculated dose was prepared at 0.2 mL/body corresponding to $1 \times 10^8$ pfu/body of a virus amount for intramuscular injection at a thigh muscle. The wild type virus (AcNPV-WT), AcNPV-PbCSPsurf (Yoshida et al. Virology 316: 161-70, 2003) or AcNPV-Dual-PbCSP was injected as the vaccine.

2. Anatomy of Mice

The mouse was euthanized three weeks after the last immunization, and serum and spleen were removed from the mouse. The serum was used for measuring the specific antibody titer and the spleen was used for ELISPOT assay.

3. Measurement of Antibody Titers

The antibody titer was measured by ELISA using a plate on which a PbCSP recombinant protein forcibly expressed in *Escherichia coli* and purified/recovered had been immobilized. The ELISA was performed according to the standard methods. As a result, although no increase of the antibody titer was identified in groups in which no virus had been inoculated or the wild type virus had been inoculated, the increase of the specific antibody titer could be identified in the group in which AcNPV-PbCSPsurf had been inoculated and the group in which AcNPV-Dual-PbCSP had been inoculated.

In FIG. 8, IgG antibody titers specific for PbCSP in the non-inoculation group, the wild type virus inoculation group, the AcNPV-PbCSPsurf inoculation group and the AcNPV-Dual-PbCSP inoculation group are shown.

4. Evaluation of Cellular Immunity Using ELISPOT Assay

ELISPOT assay was performed using spleen cells from immunized mice. The spleen cells from the mouse were prepared and an appropriate number of the cells was added to MultiScreen-IP (Millipore). A peptide (amino acid sequence: SYIPSAEKI SEQ ID NO:53) known as a CD 8 epitope of PbCSP was added thereto, which was then cultured overnight. Subsequently the reaction was performed using ELISPOT Mouse IFN-γ ELISPOT Set (BD Sciences), and a color was developed using AEC substrate set (BD Sciences). The cell number which had responded specifically for the antigen was identified by measuring colored spots. As a result, no antigen specific cell could be identified in the group in which no virus, the wild type virus or AcNPV-PbCSPsurf had been inoculated, but about 350 reacted cells per $10^6$ spleen cells were identified in the group in which AcNPV-Dual-PbCSP had been inoculated. This has demonstrated that AcNPV-Dual-PbCSP can more significantly induce the cellular immunity than AcNPV-PbCSPsurf.

In FIG. 9, the numbers of IFN-γ-producing cells specific for the CTL epitope of PbCSP in the non-inoculation group, the wild type virus inoculation group, the AcNPV-PbCSPsurf inoculation group and the AcNPV-Dual-PbCSP inoculation group are shown.

Example 10

Test for Confirming Anti-Virus Effects of Vaccine Comprising a Recombinant Baculovirus as an Active Ingredient (Test for Confirming Effects of M2e Recombinant Baculovirus)

The M2e recombinant baculovirus (AcNPV-Dual-M2e) in an amount of $3.4 \times 10^8$ PFU per mouse was inoculated in thigh muscle twice at two week interval. The mice were infected with influenza virus A/PR8/34 by inoculating 0.005 mL of solution containing 1000 $TCID_{50}$ of the virus intranasally two weeks after the final vaccine inoculation. On 6 days after the infection, the mice were euthanized, the lung was removed, and the amount of virus in the lung was detected using MDCK cells. As a result, no influenza virus could be detected in all mice inoculated with AcNPV-Dual-M2e. At the same time, this was the same effect as in the group in which the HA1 recombinant baculovirus vaccine (AcNPV-Dual-H1N1/HA1) ($1.0 \times 10^7$ PFU per mouse) had been inoculated in the thigh muscle.

In FIG. 10, intrapulmonary virus amounts 6 days after the infection with influenza virus in the PBS group, the AcNPV-Dual-M2e inoculation group and the AcNPV-Dual-H1N1/HA1 inoculation group are shown.

Example 11

Study for Identifying Preventive Effect of Pharmaceutical Containing HA1/NC99 Recombinant Baculovirus as Active Component HA1/NC99 recombinant baculovirus (AcNPV-Dual-HA1/NC99) at $1.0 \times 10^8$ PFU per mouse was inoculated in thigh muscle twice with a two week interval. Two weeks after the final inoculation, the mouse was infected with Influenza virus A/NewCaledonia/20/99 by inoculating 0.05 mL of a solution containing the virus at $1000TCID_{50}$ in a nasal cavity. Three days after the infection, the mouse was euthanized, lung was removed and the intrapulmonary virus amount was detected using MDCK cells. As a result, no influenza virus could be detected in three of four mice inoculated with AcNPV-Dual-H1N1/NC99.

In FIG. 11, the intrapulmonary virus amounts 3 days after the infection with influenza virus in the PBS group, the wild type virus (AcNPV-WT) inoculation group, and the AcNPV-Dual-HA1/NC99 inoculation group are shown.

SEQ ID NOS:25 and 26 represent the primers for identifying the expression of AcNPV-CP-H1N1/HA1, AcNPV-CAP-H1N1/HA1 and AcNPV-CU-H1N1/HA1.

SEQ ID NO:53 represent a peptide known as a CD8 epitope of PbCSP.

Example 12

Study for Identifying Specific Antibody Depending on Administration Routes of Pharmaceutical Composition Containing Recombinant Baculovirus as Active Component HA1 recombinant baculovirus (AcNPV-Dual-H1N1/HA1) at $2.0 \times 10^7$ PFU per mouse was inoculated twice with a two week interval by inoculating 0.005 mL of the virus solution in both noses (nasal drop), inoculating 0.05 mL of the virus solution from the nose (rhinovaccination), inoculating 0.05 mL of the virus solution from a respiratory tract (through the respiratory tract) and inoculating 0.05 mL of the virus solution in thigh muscle (muscular injection). Two weeks after the final inoculation, a nasal wash, an alveolar wash and serum were collected, and the expression of the antibody specific for the influenza virus was identified. The antibody titer was measured by ELISA using a plate to which an extract of MDCK cells infected with influenza virus A/PR/8/341 had been immobilized. The ELISA was performed in accordance with standard methods. As a result, the specific IgG antibody was identified in blood from the rhinovaccination group, the intratracheal vaccination group and the intramuscular vaccination group. In particular, the antibody was identified to be strongly induced in the intratracheal vaccination group. Likewise, the antigen specific IgG antibody was also identified in the nasal wash and the alveolar wash, and in particular, the antibody was strongly induced in the intratracheal vaccination group. Furthermore, in the intratracheal vaccination group, the production of antigen specific IgA antibody was also identified in the alveolar wash.

In FIG. 12, the results of ELISA measuring the IgG antibody specific for influenza virus in the blood in the nasal drop group, the rhinovaccination group, the intratracheal vaccination group and the intramuscular vaccination group are shown.

In FIG. 13, the results of ELISA measuring the IgG and IgA antibodies specific for influenza virus in the nasal wash and the alveolar wash in the nasal drop group, the rhinovaccination group, the intratracheal vaccination group and the intramuscular vaccination group are shown.

Example 13

Study for Identifying Effects Depending on Administration Routes of Pharmaceutical Composition Containing Recombinant Baculovirus as Active Component HA1 recombinant baculovirus (AcNPV-Dual-H1N1/HA1) at $1.0 \times 10^7$ PFU per mouse was inoculated twice with a two week interval by the administration route of nasal drop, rhinovaccination, through the respiratory tract or muscular injection. Two weeks after the final inoculation, the mouse was infected with influenza virus A/PR/8/34 by inoculating 0.005 mL of a solution containing the virus at $1000TCID_{50}$ in the nasal cavity. Three days after the infection, the nasal wash was collected, 6 days after the infection, the lung was removed, and the intrapulmonary virus amount was detected using MDCK cells. As a result, the virus amount in the nasal cavity 3 days after the infection was remarkably reduced in the rhinovaccination group and the intratracheal vaccination group. Furthermore, in the intratracheal vaccination group, the intrapulmonary virus amount 6 days after the infection was reduced to a detection limit or lower as well as in the intramuscular vaccination group.

In FIG. 14, the virus amounts in the nasal wash 3 days after the infection with influenza virus in the nasal drop group, the rhinovaccination group, the intratracheal vaccination group and the intramuscular vaccination group are shown.

In FIG. 15, the intrapulmonary virus amounts 6 days after the infection with influenza virus in the nasal drop group, the rhinovaccination group, the intratracheal vaccination group and the intramuscular vaccination group are shown.

Sequence Listing Free Text

SEQ ID NOS: 1 and 2 are the sequences of primers PbCSP-F and PbCSP-R1 for PCR of genomic DNA from *P. berghei* ANKA strain;

SEQ ID NOS: 3 and 4 are the sequences of primers phsp65-F1 and phsp65-R1 for PCR of genomic DNA from *M. tuberculosis* H37Rv;

SEQ ID NOS: 5 and 6 are the sequences of primers phsp65-F2 and phsp65-R2 for PCR with pcDNA as a template;

SEQ ID NOS: 7 and 8 are the sequences of primers pPolh-F2 and pgp64-R2 for PCR with pBACgus-1 (supplied from Novagen) as the template for obtaining a gp64 gene DNA fragment;

SEQ ID NOS: 9 and 10 are the sequences of primers HA-f and HA-r for PCR for producing an influenza virus HA gene fragment; and SEQ ID NOS: 11 and 12 are the sequences of primers pHA-F1 and pHA-R1 for PCR with pCR-Blunt-HA as the template.

SEQ ID NOS: 13 and 14 are the sequences of primers pTRAMP-F1 and pTRAMP-R1 for PCR of PbTRAMP gene.

SEQ ID NOS: 15 and 16 are the sequences of primers pAMA-F1 and pAMA-R1 for PCR of PbAMA1 gene domain 123 (D123).

SEQ ID NOS: 17 and 18 are the sequences of primers pMsp-F1 and pMsp-R1 for PCR of PbMSP119 gene.

SEQ ID NOS: 19 and 20 are the sequences of primers pPfCSP-F1 and pPfCSP-R1 for PCR of PfCSP gene.

SEQ ID NOS: 21 and 22 are the sequences of primers pPfAMA1-F1 and pPfAMA1-R1 for PCR of PfCSP gene from falciparum malaria parasite *P. falciparum* 3D7 strain.

SEQ ID NOS: 23 and 24 are the sequences of primers pPfs25-F1 and pPfs25-R1 for PCR of PfCSP gene from falciparum malaria parasite falciparum 3D7.

SEQ ID NOS: 25 and 26 are the sequences of primers Polh-f RsrII and GP64-r DraIII for PCR with pCR-Blunt-HA as the template.

SEQ ID NOS: 27 and 28 are the sequences of primers CMVenh-f FseI and CMVenh-r KpnI for PCR of CMV enhancer region.

SEQ ID NOS: 29 and 30 are the sequences of primers UBBp-f KpnI and UBBp-r RsrII for PCR of UBB promoter region.

SEQ ID NOS: 31 and 32 are the sequences of primers NP-f EcoRI and NP-r Cfr9I for RT-PCR of genomic RNA from influenza virus PR8/34 strain;

SEQ ID NOS: 33 and 34 are the sequences of primers M2-f EcoRI and M2-r Cfr9I for RT-PCR of genomic RNA from influenza virus PR8/34 strain;

SEQ ID NOS: 35 and 36 are the sequences of primers NAe-f EcoRI and NAe-r Cfr9I for RT-PCR of genomic RNA from influenza virus PR8/34 strain;

SEQ ID NOS: 37 and 38 are the sequences of primers M2-f EcoRI and M2e-r Cfr9I for PCR with pDual-H1N1/M2-gp64 as a template;

SEQ ID NOS: 39 and 40 are the sequences of primers HA1-f EcoRI and HA1-r CFr9I (NC99) for RT-PCR of genomic RNA from NewCaledonia99/20(NC99);

SEQ ID NOS: 41 and 42 are the sequences of primers HA0-f EcoRI and HA2-r Cfr9I for PCR with pCR-Blunt-HA as a template;

SEQ ID NOS: 43 and 44 are the sequences of primers HA2-f EcoRI and HA2-r Cfr9I for PCR with pCR-Blunt-HA as a template;

SEQ ID NOS: 45 and 46 are the sequences of primers vp39-f and vp39-r for PCR of vp39 gene region.

SEQ ID NOS: 47 and 48 are the sequences of primers Polh-S1 and HA1-r EcoRI for PCR of HA1 gene fragment.

SEQ ID NOS: 49 and 50 are the sequences of primers NP-f 5

EcoRI and NP-r EcoRI for PCR with pDual-H1N1/NP-gp64 as a template;

SEQ ID NOS: 51 and 52 are the sequences of primers for detecting expression of AcNPV-CP-H1N1/HA1, AcNPV-CAP-H1N1/HA1 and AcNPV-CU-H1N1/HA1.

SEQ ID NOS: 53 is a polypeptide which is known as CD8 epitope of PbCSP.

The invention claimed is:

1. A DNA having a molecule sequence comprising a dual promoter operatively linked to a fusion sequence, wherein the dual promoter comprises a polyhedron promoter and a CMV promoter linked to each other, and the fusion sequence encodes a malaria parasite antigen selected from the group consisting of *P. berghei* CSP, *P. falciparum* CSP, *P. falciparum* AMA1, and *P. falciparum* s25, fused to baculovirus gp64.

2. A baculovirus transfer vector comprising the DNA of claim 1.

3. A baculovirus comprising the DNA of claim 1 wherein the expressed protein from the DNA is a component of the viral particle.

4. A pharmaceutical composition comprising the baculovirus of claim 3.

5. A method of inducing an immune response against a malaria parasite protein comprising administering the pharmaceutical composition of claim 4.

* * * * *

UNITED STATES PATENT AND TRADEMARK OFFICE
CERTIFICATE OF CORRECTION

| | | |
|---|---|---|
| PATENT NO. | : 9,023,365 B2 | Page 1 of 1 |
| APPLICATION NO. | : 12/278916 | |
| DATED | : May 5, 2015 | |
| INVENTOR(S) | : Yoshida et al. | |

It is certified that error appears in the above-identified patent and that said Letters Patent is hereby corrected as shown below:

In the Claims

Column 61, line 35 delete "polyhedron promoter" and insert -- polyhedrin promoter --.

Signed and Sealed this
Twentieth Day of October, 2015

Michelle K. Lee
*Director of the United States Patent and Trademark Office*

SEQUENCE LISTING

<160> NUMBER OF SEQ ID NOS: 53

<210> SEQ ID NO 1
<211> LENGTH: 140
<212> TYPE: DNA
<213> ORGANISM: Artificial Sequence
<220> FEATURE:
<223> OTHER INFORMATION: Synthetic oligonucleotide primer

<400> SEQUENCE: 1
ggagggctag catggagaca gacacactcc tgctatgggt actgctgctc tgggttccag      60
gttccactgg tgacgcggat ccactgcagg actacaagga cgtagacaag ggatatggac     120
aaaataaagc atccaagccc                                                 140

<210> SEQ ID NO 2
<211> LENGTH: 67
<212> TYPE: DNA
<213> ORGANISM: Artificial Sequence
<220> FEATURE:
<223> OTHER INFORMATION: Synthetic oligonucleotide primer

<400> SEQUENCE: 2
ggagggcggc cgcatcccgg gttttcttat ttgaaccttt tcgttttcta actcttatac      60
cagaacc                                                                67

<210> SEQ ID NO 3
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 3
aataatagat ctaatggcca agacaattgc gtacgacgaa ga                         42

<210> SEQ ID NO 4
<211> LENGTH: 63
<212> TYPE: DNA
<213> ORGANISM: Artificial Sequence
<220> FEATURE:
<223> OTHER INFORMATION: Synthetic oligonucleotide primer

<400> SEQUENCE: 4
aatccaatgc ggccgcggga attcgattcc tgcaggtcag aaatccatgc cacccatgtc      60
gcc                                                                    63

<210> SEQ ID NO 5
<211> LENGTH: 74
<212> TYPE: DNA
<213> ORGANISM: Artificial Sequence
<220> FEATURE:
<223> OTHER INFORMATION: Synthetic oligonucleotide primer

<400> SEQUENCE: 5 caccccctgca ggactacaag gacgacgatg acaaggaatt catggccaag acaattgcgt     60
acgacgaaga ggcc                                                        74

<210> SEQ ID NO 6
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 6
cccgggcgaa atccatgcca cccatgtcgc cgccacc                                    37

<210> SEQ ID NO 7
<211> LENGTH: 48
<212> TYPE: DNA
<213> ORGANISM: Artificial Sequence
<220> FEATURE:
<223> OTHER INFORMATION: Synthetic oligonucleotide primer

<400> SEQUENCE: 7
cacccggacc ggataattaa aatgataacc atctcgcaaa taaataag                        48

<210> SEQ ID NO 8
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 8
ggtaccatat tgtctattac ggtttctaat catac                                      35

<210> SEQ ID NO 9
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 9
cctgcaggta tgaaggcaaa cctactggtc                                            30

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 10
gcccgggcga tgcatattct gca                                                   23

<210> SEQ ID NO 11
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 11
caccgaattc gacacaatat gtataggcta ccatgcg                                    37

<210> SEQ ID NO 12
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 12
cccgggcacc tctggattgg atggacggaa tg                                         32

```
<210> SEQ ID NO 13
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 13
caccgaattc aaaattgata cgaaaaaaaa tgaag                         35

<210> SEQ ID NO 14
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 14
cccgggcttt taattttgag gagtctttat tttc                          34

<210> SEQ ID NO 15
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 15
caccgaattc aatccatggg aaaagtatac ggaaaaatat                    40

<210> SEQ ID NO 16
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 16
cccgggcttc tctggtttga tgggctttca tatgcac                       37

<210> SEQ ID NO 17
<211> LENGTH: 75
<212> TYPE: DNA
<213> ORGANISM: Artificial Sequence
<220> FEATURE:
<223> OTHER INFORMATION: Synthetic oligonucleotide primer

<400> SEQUENCE: 17
caccctgcag gactacaagg acgacgatga caagcacata gcctcaatag ctttaaataa    60
cttaaataaa tctgg                                               75

<210> SEQ ID NO 18
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 18
cccgggttcc cataaagctg gaagagctac agaatacacc                    40

<210> SEQ ID NO 19
<211> LENGTH: 40
<212> TYPE: DNA
<213> ORGANISM: Artificial Sequence
```

```
<220> FEATURE:
<223> OTHER INFORMATION: Synthetic oligonucleotide primer

<400> SEQUENCE: 19
caccgaattc ttattccagg aataccagtg ctatggaagt                    40

<210> SEQ ID NO 20
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 20
cccgggcttt ttccatttta caaattttt tttc                           34

<210> SEQ ID NO 21
<211> LENGTH: 73
<212> TYPE: DNA
<213> ORGANISM: Artificial Sequence
<220> FEATURE:
<223> OTHER INFORMATION: Synthetic oligonucleotide primer

<400> SEQUENCE: 21
caccctgcag gactacaagg acgacgatga caagcagaat tattgggaac atccatatca    60
aaatagtgat gtg                                                 73

<210> SEQ ID NO 22
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 22
cccgggcttt cattttatca taagttggtt tatg                          34

<210> SEQ ID NO 23
<211> LENGTH: 43
<212> TYPE: DNA
<213> ORGANISM: Artificial Sequence
<220> FEATURE:
<223> OTHER INFORMATION: Synthetic oligonucleotide primer

<400> SEQUENCE: 23
caccgaattc aaagttaccg tggatactgt atgcaaaaga gga                43

<210> SEQ ID NO 24
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 24
cccgggcagt acatatagag ctttcattat ctat                          34

<210> SEQ ID NO 25
<211> LENGTH: 35
<212> TYPE: DNA
<213> ORGANISM: Artificial Sequence
<220> FEATURE:
<223> OTHER INFORMATION: Synthetic oligonucleotide primer
```

<400> SEQUENCE: 25
gggcggaccg gataattaaa atgataacca tctcg    35

<210> SEQ ID NO 26
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 26
gggcacttag tgatattgtc tattacggtt tctaatc    37

<210> SEQ ID NO 27
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 27
gggggccggc cctagttatt aatagtaatc aattac    36

<210> SEQ ID NO 28
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 28
gggggtaccc atggtaatag cgatgactaa tacg    34

<210> SEQ ID NO 29
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 29
gggggtacct cgaggaaggt ttcttcaact c    31

<210> SEQ ID NO 30
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 30
gggcggtccg gacctagttt aaaagtaaaa cataag    36

<210> SEQ ID NO 31
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 31
acggaattcc attcaattca aactgga    27

<210> SEQ ID NO 32
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 32
gatcccgggc cttgtcaatg ctgaatggca a            31

<210> SEQ ID NO 33
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 33
cggaattcat gagtcttcta accgagg                 27

<210> SEQ ID NO 34
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 34
gatcccgggc ctccagctct atgctgac                28

<210> SEQ ID NO 35
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 35
acggaattcc attcaattca aactgga                 27

<210> SEQ ID NO 36
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 36
gatcccgggc cttgtcaatg ctgaatggca a            31

<210> SEQ ID NO 37
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 37
cggaattcat gagtcttcta accgagg                 27

<210> SEQ ID NO 38
<211> LENGTH: 28
<212> TYPE: DNA
<213> ORGANISM: Artificial Sequence
<220> FEATURE:
<223> OTHER INFORMATION: Synthetic oligonucleotide primer

```
<400> SEQUENCE: 38
gatcccgggc atcacttgaa ccgttgca                                      28

<210> SEQ ID NO 39
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 39
gatgaattcg acacaatatg tataggctac c                                  31

<210> SEQ ID NO 40
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 40
gatcccgggc tctggattga atggatggga tg                                 32

<210> SEQ ID NO 41
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 41
ggggaattca tgaaggcaaa cctactgg                                      28

<210> SEQ ID NO 42
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 42
gatcccgggc gatgcatatt ctgca                                         25

<210> SEQ ID NO 43
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 43
gatgaattca tatttggagc cattgccg                                      28

<210> SEQ ID NO 44
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 44
gatcccgggc gatgcatatt ctgca                                         25
```

```
<210> SEQ ID NO 45
<211> LENGTH: 75
<212> TYPE: DNA
<213> ORGANISM: Artificial Sequence
<220> FEATURE:
<223> OTHER INFORMATION: Synthetic oligonucleotide primer

<400> SEQUENCE: 45
cttactagta tggactacaa ggacgacgat gacaaggaat tcggcggcgg cggctcggcg    60
ctagtgcccg tgggt                                                    75

<210> SEQ ID NO 46
<211> LENGTH: 66
<212> TYPE: DNA
<213> ORGANISM: Artificial Sequence
<220> FEATURE:
<223> OTHER INFORMATION: Synthetic oligonucleotide primer

<400> SEQUENCE: 46
cttcacttag tgatggtgat gatggtggtg cccggggctt taaagcttga cggctattcc    60
tccacc                                                              66

<210> SEQ ID NO 47
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 47
gctaaccatg ttcatgcc                                                 18

<210> SEQ ID NO 48
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 48
ggggaattca cctctggatt ggatggac                                      28

<210> SEQ ID NO 49
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 49
acggaattca tggcgtccca aggcacc                                       27

<210> SEQ ID NO 50
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 50
acggaattca ttgtcgtact cctctgcatt g                                  31
```

```
<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 51
gagctgaggg agcaattgag                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 52
gggtgatgaa taccccacag                                               20

<210> SEQ ID NO 53
<211> LENGTH: 9
<212> TYPE: PRT
<213> ORGANISM: Plasmodium berghei

<400> SEQUENCE: 53

Ser Tyr Ile Pro Ser Ala Glu Lys Ile
1               5
```